US007053264B2

(12) United States Patent
Wolffe

(10) Patent No.: US 7,053,264 B2
(45) Date of Patent: May 30, 2006

(54) NUCLEAR REPROGRAMMING USING IWSI AND RELATED CHROMATIN REMODELING ATPASES

(75) Inventor: Alan P. Wolffe, deceased, late of Orinda, CA (US); by Elizabeth Wolffe, legal representative, Orinda, CA (US)

(73) Assignee: Sangamo Biosciences, Inc., Richmond, CA (US)

( * ) Notice: Subject to any disclaimer, the term of this patent is extended or adjusted under 35 U.S.C. 154(b) by 242 days.

(21) Appl. No.: 09/967,868

(22) Filed: Sep. 28, 2001

(65) Prior Publication Data

US 2002/0094968 A1    Jul. 18, 2002

Related U.S. Application Data

(60) Provisional application No. 60/236,409, filed on Sep. 28, 2000.

(51) Int. Cl.
C12N 15/00 (2006.01)
C12N 15/02 (2006.01)
A01N 1/00 (2006.01)

(52) U.S. Cl. .......................... 800/24; 800/21; 435/1.1; 435/449

(58) Field of Classification Search ................ 800/24, 800/21; 435/449, 1.1
See application file for complete search history.

(56) References Cited

U.S. PATENT DOCUMENTS 6,011,197 A    1/2000   Strelchenko et al.

FOREIGN PATENT DOCUMENTS

WO    WO 01/68831 A2    9/2001
WO    WO 01/83793 A2    11/2001

OTHER PUBLICATIONS

Campbell. Cloning & Stem Cells, 3(4):201-208 (2001).*
Dinnyés et al. Cloning & Stem Cells, 4(1): 81-90 (2002).*
Pennisi and Vogel. Science, 288:1722-1727 (2000).*
Yamagimachi et al. Mol. And Cell. Endocrin., 187:241-248 (2002).*
Vogel. Science, 300:226-227 (2003).*
Fehilly et al. Nature, vol. 307 (1984).*
DiBerardino et al. PNAS, 83:8231-8234 (1986).*
Westhusin et al. Theriogenology, vol. 55, pp. 35-49, 2001.*
Bochar et al., "A Family of Chromatin Remodeling Factors Related To Williams Syndrome Transcription Factor," *PNAS USA* 97(3):1038-1043 (2002).
Cairnes, "Chromatin Remodeling Machines: Similar Motors, Ulterior Motives," *Trends Biochem. Sci.* 23:20-25 (1998).

Chan et al., "Nuclear Transplantation from Stably Transfected Cultured Cells of *Xenopus*," *Intl. J. Dev. Biol.* 40:441-451 (1996).
Corona t al., "ISWI is a ATP-Dependent Nucleos me Remodeling Fact r," *Molecular Cell* 3(2):239-245 (1999).
de La Serna et al., "Mammalian SWI-SNF Complexes Contribute to Activation of the *hsp70* Gene," *Molecular and Cellular Biolology* 20:2839-2851 (2000).
Deuring et al., "The ISWI Chromatin-Remodeling Protein is Required for Gene Expression and the Maintenance of Higher Order Chromatin Structure *In Vivo*," *Mol. Cell* 5:355-365 (2000).
Fryer et al., "Chromatin Remodelling by the Glucocorticoid Receptor Requires the BRG1 Complex," *Nature* 393:88-91 (1998).
Gurdon, "Adult Frogs Derived From the Nuclei of Single Somatic Cells," *Dev. Biol.* 4:256-273 (1962).
Gurdon et al., "The Future of Cloning," *Nature* 402:743-746 (1999).
Gurdon et al., "Injected Nucleic in Frog Oocytes: RNA Synthesis and Protein Exchange," *J. Embryol. Exp. Morphol.* 36:541-553 (1976).
Gurdon et al., "Reprogramming of Transplanted Nuclei in Amphibia," *Int. Rev. Cyto Suppl.* 9:161-178 (1979).
Holsteege et al., "Dissecting the Regulatory Circuitry of a Eukaryotic Genome," *Cell* 95:717-728 (1998).
Jeddeloh et al.,"Maintenance of Genomic Methylation Requires a SW12/SNF2-Like Protein," *Nat. Genet.* 22:94-97 (1999).
Kato et al., "Eight Calves Cloned From Somatic Cells of a Single Adult," *Science* 282:2095-2098 (1998).
Kingston et al., "ATP-Dependent Remodeling and Acetylation as Regulators of Chromatin Fluidity," *Genes and Devel.* 13:2339-2352 (1999).
Murchardt et al., "ATP-Dependent Chromain Remodeling: SWI/SNF and Co. are on the Job," *J. Mol. Biol.* 293:185-197 (1999).
Sudarsanam et al., "Whole-Genome Expression Analysis of SNF/SWI Mutants of *Saccharomyces Cerevisiae*," *Proc. Natl.. Acad. Sci. USA* 97:3364-3369 (2000).
Tada et al., "Embryonic Germ Cells Induce Epigenetic Reprogramming of Somatic Nucleus in Hybrid Cells," *EMBO J.* 16(21):6510-6520 (1997).

(Continued)

*Primary Examiner*—Joseph Woitach
(74) *Attorney, Agent, or Firm*—Robins & Pasternak LLP; Sean M. Brennan

(57) ABSTRACT

Methods and compositions for dedifferentiating nuclei from somatic cells are provided. Such methods and compositions are useful for facilitating processes such as, for example, cloning and immortalization of cells.

10 Claims, 3 Drawing Sheets

OTHER PUBLICATIONS

Wakayama et al., "Full-Term Development of Mice from Enucleated Oocytes Injected With Cumulus Cell Nuclei," *Nature 394*:369-374 (1998).

Wilmut et al., "Viable Offspring Derived from Fetal and Adult Mammalian Cells," *Nature 385*:810-813 (1997).

Workman et al., "Alteration of Nucleosome Structure As a Mechanism of Transcriptional Regulation," *Ann. Rev. Biochem. 67*:545-579 (1998).

Kikyo et al. (2000) "Active remodeling of somatic nuclei in egg cytoplasm by the nucleosomal ATPase ISWI", *Science*, 289(5488): 2360-2362.

Kikyo et al. (2000) "Reprogramming nuclei: insights from cloning, nuclear transfer and heterokaryons", *Journal of Cell Science*, 113(1): 11-20.

* cited by examiner

NUCLEAR REPROGRAMMING USING IWSI AND RELATED CHROMATIN REMODELING ATPASES

CROSS-REFERENCE TO RELATED APPLICATIONS

This application is related to provisional patent application Ser. No. 60/236,409, filed Sep. 28, 2000, from which priority is claimed under 35 USC §119(e) and which application is incorporated herein by reference in its entirety.

TECHNICAL FIELD

The present disclosure is in the fields of cloning and nuclear reprogramming, using compositions comprising the ISWI protein or a related chromatin remodeling ATPase to modulate gene expression and cellular differentiation, and to facilitate cloning and nuclear transfer.

BACKGROUND

The nature and function of any given cell depends on the particular set of genes being expressed (e.g., transcribed and translated). Thus, development of pluripotent or totipotent cells into a differentiated, specialized phenotype is determined by the particular genes expressed during development. Gene expression is directly mediated by sequence-specific binding of gene regulatory proteins that can effect either positive or negative regulation. However, the ability of any of these regulatory proteins to directly mediate gene expression appears to depends on the accessibility of their binding site within the cellular DNA. Accessibility of sequences in cellular DNA often depends on the structure of cellular chromatin within which cellular DNA is packaged.

Cellular DNA, including the cellular genome, generally exists in the form of chromatin, a complex comprising nucleic acid and protein. Indeed, most cellular RNAs also exist in the form of nucleoprotein complexes. The nucleoprotein structure of chromatin has been the subject of extensive research, as is known to those of skill in the art. In general, chromosomal DNA is packaged into nucleosomes. A nucleosome comprises a core and a linker. The nucleosome core comprises an octamer of core histones (two each of H2A, H2B, H3 and H4) around which is wrapped approximately 150 base pairs of chromosomal DNA. In addition, a linker DNA segment of approximately 50 base pairs is associated with linker histone H1. Nucleosomes are organized into a higher-order chromatin fiber and chromatin fibers are organized into chromosomes. See, for example, Wolffe "Chromatin: Structure and Function" 3$^{rd}$ Ed., Academic Press, San Diego, 1998.

The structure of chromatin can be altered through the activity of macromolecular assemblies known as chromatin remodeling complexes. See, for example, Cairns (1998) Trends Biochem. Sci. 23:20–25; Workman et al. (1998) Ann. Rev. Biochem. 67:545–579; Kingston et al. (1999) Genes Devel. 13:2339–2352 and Murchardt et al. (1999) J. Mol. Biol. 293:185–197. Recently, chromatin remodeling complexes have been implicated in the disruption or reformation of nucleosomal arrays, resulting in modulation of transcription, DNA replication, and DNA repair. Bochar et al. (2000) PNAS USA 97(3): 1038–43. Many of these chromatin remodeling complexes have different subunit compositions, but all rely on ATPase enzymes for remodeling activity. There are also several examples of a requirement for the activity of chromatin remodeling complexes for gene activation in vivo. The human SWI/SNF chromatin remodeling complex is required for the activity of the glucocorticoid receptor. Fryer et al. (1998) Nature 393:88–91. The mammalian SWI/SNF chromatin remodeling complex is required for activation of the hsp70 gene. de La Serna et al (2000) Mol. Cell. Biol. 20:2839–2851. In addition, mutations in the yeast SWI/SNF gene result in a decrease in expression of one group of genes and an increase in expression of another group of genes, showing that chromatin remodeling can have both positive and negative effects on gene expression. Holsteege et al. (1998) Cell 95:717–728; Sudarsanam et al. (2000) Proc. Natl. Acad. Sci. USA 97:3364–3369.

It has also been shown that mutations in the Drosophila ISWI protein adversely affect expression of the engrailed and Ultrabithorax genes. Deuring et al. (2000) Mol. Cell 5:355–365. The ATPase ISWI is a subunit of several distinct nucleosome remodeling complexes that increase the accessibility of DNA in chromatin (Corona et al. (1999) Mol Cell 3(2):239–245). Isolated ISWI protein has been shown to carry out nucleosome remodeling, nucleosome rearrangement, and chromatin assembly reactions (Corona et al., supra). The ATPase activity of ISWI is stimulated by nucleosomes but not by free DNA or free histones, indicating that ISWI recognizes a specific structural feature of nucleosomes. Nucleosome remodeling by ISWI, therefore, does not require a functional interaction between ISWI and the other subunits of ISWI complexes.

Successful cloning of frogs and several mammalian species by nuclear transplantation has been reported (Gurdon (1962) Dev Biol 4:256–273; Wilmut et al. (1997) Nature 385:810–813; Wakayama et al. (1998) Nature 394:369–374; Kato et al. (1998) Science 282:2095–2098), establishing the remarkable reversibility of the genetic and epigenetic programs that define cell differentiation. Even highly differentiated somatic nuclei can dedifferentiate in egg cytoplasm to acquire the totipotency essential to support normal development to reproductive adulthood. However, despite the ability to generate adult animals from transplanted somatic nuclei, the process is extremely inefficient. See, e.g., Gurdon et al. (1999) Nature 402:743–746. Methods and compositions to increase the efficiency of cloning by nuclear transplantation would clearly advance the field.

The ability of a somatic nucleus to program the development of an entire organism indicates that a somatic nucleus can be dedifferentiated in the egg cytoplasm. Patterns of gene expression in embryos derived from adult nuclei several hours after their transplantation into eggs are indistinguishable from the patterns of normal embryos at the same developmental stage. Chan et al. (1996) Intl. J. Dev. Biol. 40:441–451. This result indicates that nuclear reprogramming is manifested, at least in part, by changes in gene expression that likely result from the change in cytoplasmic environment experienced by the somatic nucleus. This dedifferentiation of a somatic nucleus by egg cytoplasm may be mediated by gain and/or loss of proteins which directly or indirectly affect gene expression. Indeed, somatic nuclei transplanted into Xenopus eggs lose more than 85% of radiolabeled nuclear protein concomitant with substantial uptake of proteins from the egg cytoplasm (Gurdon et al. (1976) J Embryol Exp Morphol 36:541–553; Gurdon et al. (1979) Int Rev Cyto Suppl 9:161–178). Transplanted nuclei might lose preexisting chromatin binding proteins passively through dilution during DNA replication in the comparatively large volume of the egg/embryo cytoplasm. However, emerging evidence suggests that reprogramming of epigenetic states can occur in the nuclei of differentiated cells following heterokaryon formation with stem cells, a process in which dilution does not occur (Tada et al. (1997) *EMBO J* 16:6510–6520). Thus, it is possible that nuclear reprogramming is mediated by remodeling of nuclear chromatin. In support of this idea, it has been found that both local remodeling of chromatin and alterations in DNA methylation states, events which result in dramatic changes in the functionality of DNA, leading to alterations in gene activity and cell physiology, require the activity of nucleosomal ATPases (Jeddeloh et al. (1999) *Nat Genet* 22:94–97).

Whether differentiated nuclei undergo specific or global chromatin remodeling activities upon transplantation into eggs, and/or whether chromatin remodeling occurs during generation of stem cell lineages is not well studied. Gurdon et al. (1999) supra. It is possible that some sort of reprogramming or global chromatin remodeling would increase the success rate of cloning by nuclear transplantation Thus, new methods of gene regulation and nuclear reprogramming, that utilize the activity of chromatin remodeling complexes and/or enzymatic chromatin remodeling proteins, would facilitate, among other things, cloning and modulation of cellular differentiation and dedifferentiation.

SUMMARY

Compositions and methods for reprogramming nuclei using ISWI and related chromatin remodeling ATPases are provided. In one aspect, methods for facilitating cloning, particularly cloning of animals, are provided. In certain embodiments, the methods comprise: (a) contacting a somatic nucleus with a composition comprising ISWI, wherein the composition remodels the somatic nucleus; and (b) introducing the somatic nucleus of step (a) into an enucleated oocyte. The ISWI can be provided as a polypeptide or as a polynucleotide. In some embodiments, the contacting is in vitro and in other embodiments, the contacting is in vivo. In yet other embodiments, the somatic nucleus and the enucleated oocyte are both derived from an animal, for example a human or a domestic animal such as a sheep, cow or pig.

Also provided are methods for facilitating dedifferentiation of a target cell, the method comprising the step of contacting the cell with a composition comprising ISWI. The ISWI can be provided as a polypeptide or as a polynucleotide. In some embodiments, the contacting is in vitro and in other embodiments, the contacting is in vivo. The cell can be a prokaryotic cell or a eukaryotic cell, for example a plant cell or an animal cell (e.g., a human cell or a cell from a domestic animal such as a sheep, cow or pig). The contacting of the ISWI with the target cell can be in vitro or in vivo.

Methods of facilitating differentiation of a target cell are also provided. The methods entail, for example, contacting the target cell with a composition comprising an ISWI-inhibitor. In some embodiments, the contacting is in vitro and in other embodiments, the contacting is in vivo. The cell can be a prokaryotic cell or a eukaryotic cell, for example a plant cell or an animal cell (e.g., a human cell or a cell from a domestic animal such as a sheep, cow or pig). In some embodiments, the target cell si a neoplastic cell. The contacting of the ISWI with the target cell can be in vitro or in vivo. Furthermore, the ISWI-inhibitor can be an antibody or other small molecule.

Also provided herein are methods of facilitating nuclear transplantation, the method comprising the step of contacting a somatic nucleus with a composition comprising ISWI. The ISWI can be provided as a polypeptide or as a polynucleotide. In some embodiments, the contacting is in vitro and in other embodiments, the contacting is in vivo. The cell can be a prokaryotic cell or a eukaryotic cell, for example a plant cell or an animal cell (e.g., a human cell or a cell from a domestic animal such as a sheep, cow or pig). The contacting of the ISWI with the target cell can be in vitro or in vivo.

These and other embodiments will be readily apparent to one of skill in the art in view of the teachings herein.

BRIEF DESCRIPTION OF THE DRAWINGS

FIG. 1A shows immunoblots for TBP, ORC2 and histone H2b; the results indicate that TBP is actively removed from somatic nuclei during incubation in an egg extract. Lanes contain: precipitated material from the egg extract (lane 1), 4 µl of the total egg extract (lane 2), $1\times10^5$ nuclei (lane 3), remodeled nuclei isolated from the reaction mix (lane 4); the remaining lanes show nuclear remodeling conducted in the presence of 10 units/ml of apyrase (lane 5), 2 mM AMP-PNP (lane 6), 2 mM GMP-PNP (lane 7), 150 µM aphidicholin (lane 8) or 200 µM AraC (lane 9). Lanes 4 and 6–9 contained an energy regenerating system (ERS). FIG. 1B show immunoblotting analysis of TFIIB, nucleolin and histone H1; the results indicate that a subset of nuclear proteins are depleted from the nuclei. FIG. 1C shows immunoblots for TFIIF, ISWI, nucleoplasmin and egg-specific linker histone B4; the results indicate that certain proteins initially present in the egg extract accumulate in the nuclei. FIG. 1D shows immunoblots fro MeCP2, TopoII, Rpd3, Sin3 and RNA polymerase II, examples of nuclear proteins which resist repartitioning. Lane contents in FIGS. 1B–1D are the same as those in FIG. 1A.

FIG. 2A shows analysis using an anti-TBP antibody. FIG. 2B shows analysis using an anti-ISWI antibody. The bar represents 15 µm and arrow heads indicate the nucleoli. The results of this analysis indicate that redistribution of proteins is accompanied by changes in nuclear structure.

FIG. 4A shows purification of Xenopus ISWI-D. Fractions containing ISWI were analyzed by immunoblot analysis. "Extract" refers to unfractionated egg extract. FIG. 4B shows SDS-PAGE of purified ISWI-D and rISWI. The gel was stained with Coomassie Blue. FIG. 4C depicts ATPase activity of ISWI-D and rISWI. ATPase activity was determined in the presence of buffer (–), DNA (D), or nucleosomes (N). The arrowhead indicates the free phosphate generated by ATP hydrolysis. FIG. 4D depicts biochemical complementation assays for activities capable of removing TBP from the nucleus. Egg extract (Ext), SP Sepharose flow through (FT), and FT complemented with various purified proteins at indicated concentrations were compared for remodeling activity by monitoring residual TBP in the nuclear pellet after incubation of nuclei in an egg extract. All lanes included ERS except lanes 7 and 8, which contained apyrase. Np indicates nucleoplasmin.

DETAILED DESCRIPTION

Figure 1:
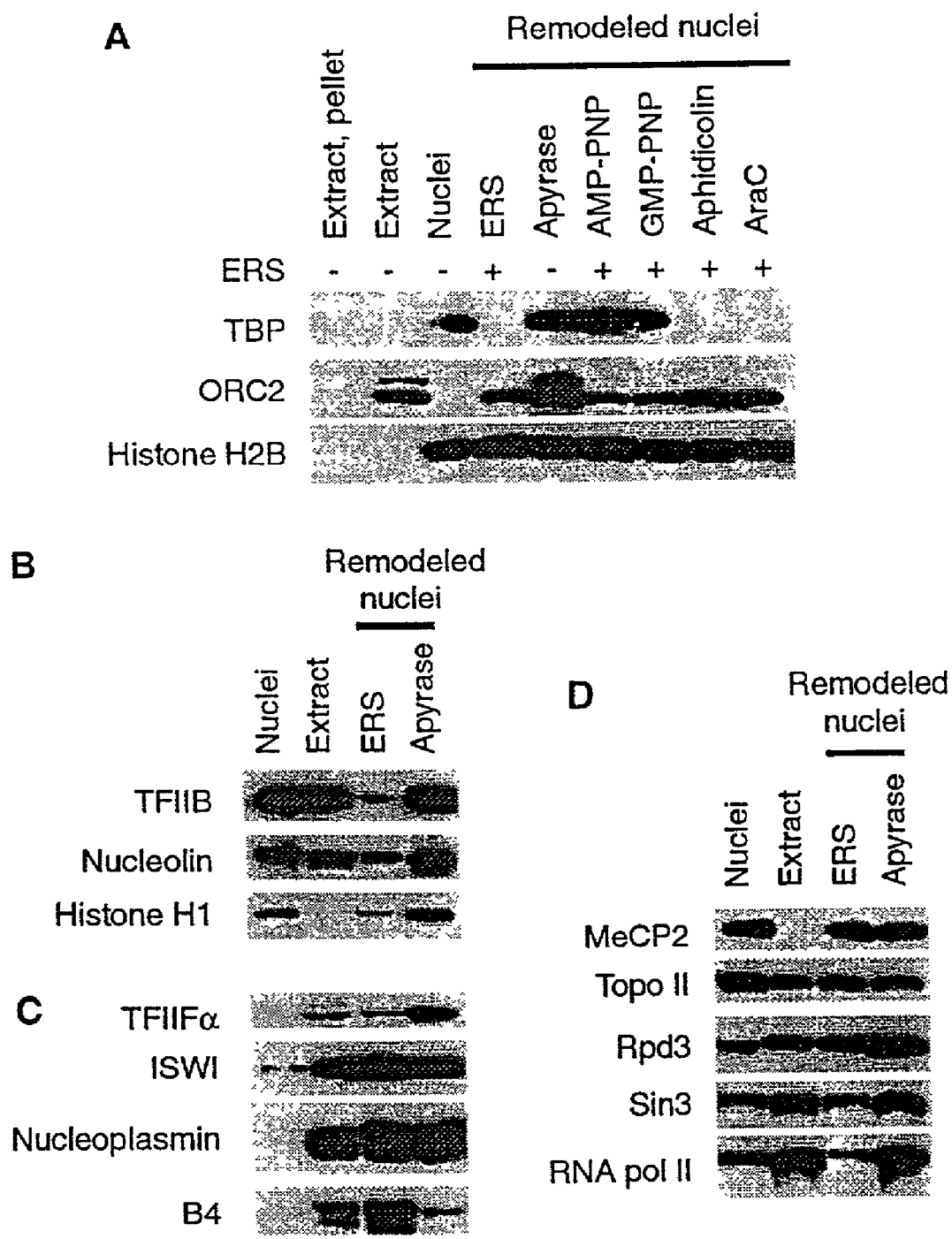
FIGS. 1A–D show analysis of proteins in somatic nuclei that have been incubated in egg extracts.

Disclosed herein are compositions and methods, particularly ISWI-containing compositions, useful for (1) modulating differentiation or dedifferentiation of a target cell; (2) facilitating cloning and transfection efficiency into a target cell and (3) modulating gene expression.

In one aspect, compositions and methods useful for dedifferentating somatic cell nuclei are provided. Previous experiments involving the transfer of nuclei from differentiated cells into eggs or egg extracts have indicated that protein exchange may be mechanistically involved in nuclear remodeling processes that result in the generation of a nuclear transplant clone. Gurdon et al. (1976) supra; Gurdon et al. (1979) supra. Described herein is the identification of an energy dependent system, including the protein ISWI, that is capable of removal of chromosomal proteins from somatic nuclei and reversal of their interaction with chromosomal DNA.

Thus, the methods and compositions disclosed herein allow for reprogramming (e.g., dedifferentiation) of a somatic nucleus, by employing a composition comprising one or more chromatin remodeling ATPases and/or associated proteins. The ATPase(s) can be selected for their ability to regulate gene expression, for example by actively removing transcription factors such as the TATA binding protein (TBP) from their associations with chromatin and/or the nuclear matrix. Any chromatin remodeling protein (or complex) having the requisite specificity is suitable. In a preferred embodiment, the nucleosomal remodeling protein (or complex) comprises ISWI which, in the presence of an energy regeneration system (ERS), actively reverses binding of the transcription factor TBP to cellular chromatin. In addition, ISWI is capable of reducing the levels of chromatin-bound linker histone H1, nucleolin, and the general transcription factor TFIIB , in the presence of an ERS. Thus, the chromatin remodeling protein(s) (or complex) are able to modulate gene expression and dedifferentiation, by modulating the association of transcription factors with cellular chromatin.

The methods and compositions described herein also allow for increased ease and efficiency in cloning and transfection. For example, cloning of domestic animals has typically been attempted by transplanting a somatic nucleus into an enucleated oocyte. Such nuclear transplant techniques have a low success rate, presumably because the enucleated oocyte must contain all the components necessary to remodel and reprogram the somatic DNA such that a live born animal is obtained. Therefore, using the compositions and methods described herein, somatic nuclei can be remodeled (e.g., partially or fully dedifferentiated) prior to being transferred into the enucleated oocyte, thereby increasing the likelihood of a live birth.

It will be apparent to one of skill in the art that nucleosomal remodeling protein(s) will facilitate the regulation of many processes involving gene expression including, but not limited to, embryonic development, replication, recombination, repair, transcription, telomere function and maintenance, sister chromatid cohesion, mitotic chromosome segregation and, in addition, binding of transcription factors.

General

The practice of the invention employs, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

All patents, patent applications, and publications mentioned herein, whether supra or infra, are hereby incorporated by reference in their entirety.

Definitions

The terms "nucleic acid," "polynucleotide," and "oligonucleotide" are used interchangeably and refer to a deoxyribonucleotide or ribonucleotide polymer in either single- or double-stranded form. When not used to refer to a nucleic acid obtained from an organism, the term can encompass known analogues of natural nucleotides, as well as nucleotides that are modified in the base, sugar, and/or phosphate moieites.

Chromatin is the nucleoprotein structure comprising the cellular genome. "Cellular chromatin" comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and a segment of linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome" is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

The term "totipotent" refers to a cell in a developing cell mass such as, for example, an embryo or a fetus, that can potentially give rise to all of the cells in an adult organism,.

The term "pluripotent" refers to a cell that can differentiate into many, but not all of the cell types of an adult organism.

The term "differentiated cell" refers to a cell that has developed from a relatively unspecialized phenotype to a more specialized phenotype. For example, a progenitor cell type such as a hematopoietic stem cell can give rise to a more differentiated cell such as a monocyte or an erythrocyte. The term "dedifferentiated cell" refers to a cell that had formerly attained a particular degree of differentiation, but has subsequently been immortalized or regained the ability to differentiate into one or more specialized cells (e.g., has become pluripotent or totipotent). It is highly unlikely that differentiated cells will revert into their precursor cells (i.e., dedifferentiate) in vivo or in vitro. However, using the method and compositions described herein, differentiated cells can be reprogrammed into immortalized, pluripotent or totipotent cells. Differentiated cells can be isolated from embryonic or somatic cells using techniques known in the art.

The terms "convert," "reprogram" and "dedifferentiate" are used interchangeably to refer to the phenomenon in which a differentiated cell becomes immortalized, pluripotent and/or totipotent. Cells can be dedifferentiated or converted to varying degrees. For example, it is possible that only a small portion of cells are converted or that an individual cell is reprogrammed to be pluripotent but not necessarily totipotent. Thus, the terms "converting," "reprogramming" or "dedifferentiating" compositions refer to compositions such as, for example, ISWI which are able to dedifferentiate a target cell by actively remodeling chromatin and reversing binding of transcription factors. Alternatively, a "converting," "reprogramming" or "dedifferentiating" composition can facilitate the binding of one or more transcription factors or chromosomal proteins to cellular chromatin.

An "episome" is a replicating nucleic acid, nucleoprotein complex or other structure comprising a nucleic acid that is not part of the chromosomal karyotype of a cell. Examples of episomes include plasmids and certain viral genomes.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Gene activation" and "augmentation of gene expression" refer to any process which results in an increase in production of a gene product. A gene product can be either RNA (including, but not limited to, mRNA, rRNA, tRNA, and structural RNA) or protein. Accordingly, gene activation includes those processes which increase transcription of a gene and/or translation of a mRNA. Examples of gene activation processes which increase transcription include, but are not limited to, those which facilitate formation of a transcription initiation complex, those which increase transcription initiation rate, those which increase transcription elongation rate, those which increase processivity of transcription and those which relieve transcriptional repression (by, for example, blocking the binding of a transcriptional repressor). Gene activation can constitute, for example, inhibition of repression as well as stimulation of expression above an existing level. Examples of gene activation processes which increase translation include those which increase translational initiation, those which increase translational elongation and those which increase mRNA stability. In general, gene activation comprises any detectable increase in the production of a gene product, preferably an increase in production of a gene product by about 2-fold, more preferably from about 2- to about 5-fold or any integer therebetween, more preferably between about 5- and about 10-fold or any integer therebetween, more preferably between about 10- and about 20-fold or any integer therebetween, still more preferably between about 20- and about 50-fold or any integer therebetween, more preferably between about 50- and about 100-fold or any integer therebetween, more preferably 100-fold or more.

"Gene repression" and "inhibition of gene expression" refer to any process which results in a decrease in production of a gene product. A gene product can be either RNA (including, but not limited to, mRNA, rRNA, tRNA, and structural RNA) or protein. Accordingly, gene repression includes those processes which decrease transcription of a gene and/or translation of a mRNA. Examples of gene repression processes which decrease transcription include, but are not limited to, those which inhibit formation of a transcription initiation complex, those which decrease transcription initiation rate, those which decrease transcription elongation rate, those which decrease processivity of transcription and those which antagonize transcriptional activation (by, for example, blocking the binding of a transcriptional activator). Gene repression can constitute, for example, prevention of activation as well as inhibition of expression below an existing level. Examples of gene repression processes which decrease translation include those which decrease translational initiation, those which decrease translational elongation and those which decrease mRNA stability. Transcriptional repression includes both reversible and irreversible inactivation of gene transcription. In general, gene repression comprises any detectable decrease in the production of a gene product, preferably a decrease in production of a gene product by about 2-fold, more preferably from about 2- to about 5-fold or any integer therebetween, more preferably between about 5- and about 10-fold or any integer therebetween, more preferably between about 10- and about 20-fold or any integer therebetween, still more preferably between about 20- and about 50-fold or any integer therebetween, more preferably between about 50- and about 100-fold or any integer therebetween, more preferably 100-fold or more. Most preferably, gene repression results in complete inhibition of gene expression, such that no gene product is detectable.

"Eucaryotic cells" include, but are not limited to, fungal cells (such as yeast), plant cells, animal cells, mammalian cells and human cells.

The terms "operative linkage" and "operatively linked" are used with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. An operatively linked transcriptional regulatory sequence is generally joined in cis with a coding sequence, but need not be directly adjacent to it. For example, an enhancer can constitute a transcriptional regulatory sequence that is operatively-linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to a transcriptional activation domain (or functional fragment thereof), the ZFP DNA-binding domain and the transcriptional activation domain (or functional fragment thereof) are in operative linkage if, in the fusion polypeptide, the ZFP DNA-binding domain portion is able to bind its target site and/or its binding site, while the transcriptional activation domain (or functional fragment thereof) is able to activate transcription.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one ore more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. See Ausubel et al., supra. The ability of a protein to interact with another protein can be determined, for example, by co-immunoprecipitation, two-hybrid assays or complementation, both genetic and biochemical. See, for example, Fields et al. (1989) Nature 340:245–246; U.S. Pat. No. 5,585,245 and PCT WO 98/44350.

The term "recombinant," when used with reference to a cell, indicates that the cell replicates an exogenous nucleic acid, or expresses a peptide or protein encoded by an exogenous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

A "recombinant expression cassette" or simply an "expression cassette" is a nucleic acid construct, generated recombinantly or synthetically, that has control elements that are capable of effecting expression of a structural gene that is operatively linked to the control elements in hosts compatible with such sequences. Expression cassettes include at least promoters and optionally, transcription termination signals. Typically, the recombinant expression cassette includes at least a nucleic acid to be transcribed (e.g., a nucleic acid encoding a desired polypeptide) and a promoter. Additional factors necessary or helpful in effecting expression can also be used as described herein. For example, an expression cassette can also include nucleotide sequences that encode a signal sequence that directs secretion of an expressed protein from the host cell. Transcription termination signals, enhancers, and other nucleic acid sequences that influence gene expression can also be included in an expression cassette.

The term "naturally occurring," as applied to an object, means that the object can be found in nature.

The terms "polypeptide," "peptide" and "protein" are used interchangeably to refer to a polymer of amino acid residues. The term also applies to amino acid polymers in which one or more amino acids are chemical analogues of a corresponding naturally-occurring amino acids.

A "subsequence" or "segment" when used in reference to a nucleic acid or polypeptide refers to a sequence of nucleotides or amino acids that comprise a part of a longer sequence of nucleotides or amino acids (e.g., a polypeptide), respectively.

The term "antibody" as used herein includes antibodies obtained from both polyclonal and monoclonal preparations, as well as, the following: (i) hybrid (chimeric) antibody molecules (see, for example, Winter et al. (1991) Nature 349:293–299; and U.S. Pat. No. 4,816,567); (ii) F(ab')2 and F(ab) fragments; (iii) Fv molecules (noncovalent heterodimers, see, for example, Inbar et al. (1972) Proc. Natl. Acad. Sci. USA 69:2659–2662; and Ehrlich et al. (1980) Biochem 19:4091–4096); (iv) single-chain Fv molecules (sFv) (see, for example, Huston et al. (1988) Proc. Natl. Acad. Sci. USA 85:5879–5883); (v) dimeric and trimeric antibody fragment constructs; (vi) humanized antibody molecules (see, for example, Riechmann et al. (1988) Nature 332:323–327; Verhoeyan et al. (1988) Science 239:1534–1536; and U.K. Patent Publication No. GB 2,276, 169, published Sep. 21, 1994); (vii) Mini-antibodies or minibodies (i.e., sFv polypeptide chains that include oligomerization domains at their C-termini, separated from the sFv by ahinge region; see, e.g., Pack et al. (1992) Biochem 31:1579–1584; Cumber et al. (1992) J. Immunology 149B: 120–126); and, (vii) any functional fragments obtained from such molecules, wherein such fragments retain specific-binding properties of the parent antibody molecule.

"Specific binding" between an antibody or other binding agent and an antigen, or between two binding partners, means that the dissociation constant for the interaction less than $10^{-6}$ M. Preferred antibody/antigen or binding partner complexes have a dissociation constant of less than about $10^{-7}$ M, and preferably $10^{-8}$ M to $10^{-9}$ M or $10^{-10}$ M.

Modulation of Cellular Differentiation Using ISWI-Containing Compositions

A. Chromatin Remodeling Proteins and Complexes

There are essentially two major types of chromatin modification carried out in vivo by multiprotein complexes. The first major type is dependent on covalent modification of histones which occurs by processes such as, for example, acetylation and deacetylation. Covalent modification of DNA is exemplified by methylation of cytosine residues in CpG dinucleotides. The second type of modification is known to result in changes in nucleosome location and/or conformation, and relies on the activity of ATP-driven chromatin remodeling machines. Multiprotein chromatin remodeling complexes which exhibit one or more of the foregoing activities (e.g., nucleosome-, histone- and/or DNA-dependent ATPase activity) and catalyze various types of modification of chromatin structure generally comprise an enzymatic component (an ATPase protein subunit) and one or more non-enzymatic protein subunits.

ATPase subunits are further grouped into three major families: the SWI/SNF family, the ISWI family, and the Mi-2/CHD family. See Tyler et al. (1999) *Cell* 99:443–446. Other enzymatic components of chromatin remodeling complexes include, but are not limited to, the following ATPases: SWI2/SNF2, STH1, BRM, hBRM, BRG1, Mi2/CHD, ISW2, and hSNF2h. Tyler et al., supra; Armstrong et al. (1998) *Curr. Opin. Genet. Dev.* 8:165–172; Guschin et al (1999) *Curr. Biol.* 9:R742–746; and Wolffe et al. (2000) *J. Struct. Biol.* 129:102–122.

The ISWI ATPase was initially identified as a homologue to the yeast SWI2/SNF2 chromatin remodeling ATPase. Accordingly, the SWI2/SNF2 ATPase, and related chromatin remodeling proteins, are also useful in the methods and compositions disclosed herein. Furthermore, additional ISWI homologues and related proteins have been identified; these are also useful in the disclosed methods and compositions. ISWI homologues and related proteins include, but are not limited to, human hSNF2h (also known as WCRF 135), yeast ISW1 and yeast ISW2. Additional ISWI homologues, and/or modified versions of ISWI and/or ISWI-related proteins, are available to those of skill in the art, using known techniques of mutagenesis, protein modification, functional assays, and homology searching.

However, prior to the present disclosure, it was not known what role, if any, these proteins (or multiprotein complexes) played in reprogramming transplanted somatic nuclei. Described herein is the novel finding that the chromatin remodeling protein ISWI is able to remodel somatic nuclei and reverse binding of one or more transcription factors to cellular DNA. Accordingly, in preferred embodiments, the chromatin remodeling complex comprises a member of the ISWI family that is able to remodel somatic nuclei, for example by reversing binding of one or more transcription factors. Suitable ISWI-containing compositions can comprise one of its constituent proteins or a functional fragment thereof.

In addition to facilitating dedifferentiation of somatic nuclei, the compositions and methods described herein may also modify chromatin, for example, to render chromosomal sequences more accessible to regulatory factors (i.e., formation of "open" chromatin) or to make chromosomal sequences less accessible (i.e., formation of "closed" chromatin). Such modifications can include, for example, removal of nucleosomes from DNA, deposition of nucleosomes onto DNA, repositioning of nucleosomes, changes in nucleosome spacing, changes in nucleosome density, changes in the degree and/or nature of the interaction between DNA and histones in the nucleosome, changes in the path of DNA along the surface of the nucleosome, and/or changes in higher-order chromatin structure such as, for example, unwinding of the chromatin solenoid.

The present inventors have demonstrated that chromatin remodeling proteins such as, for example, ISWI and related proteins, are major contributors to the active, highly specific and extraordinarily efficient removal of key regulatory components such as TBP from somatic nuclei in the egg environment. The surprising and unexpected discovery that ISWI actively erases transcription factor binding in transplanted nuclei allows for the design of systems which modulate cellular differentiation (i.e., facilitate dedifferentiation), facilitate cloning, transfection and establishment of immortalized and/or stem cell lineages. Alternatively, inhibitors of IWSI function can be used to promote differentiation, for example, in hyperproliferative, dedifferentiated cells.

B. Dedifferentiation

ISWI's ability to modulate gene expression by actively removing TBP from association with the nuclear matrix has profound implications for development of in vitro and in vivo systems of dedifferentiation. Thus, in certain embodiments, compositions comprising ISWI, ISWI-related proteins or functional equivalents (also referred to as "dedifferentiating compositions") are provided to a target cell or nucleus in an amount effective to reprogram the target cell or nucleus from a differentiated to a dedifferentiated state. The amount or concentration of dedifferentiating composition necessary to achieve the desired effect can be readily determined by one of skill in the art in view of the teachings herein.

Target cells include, but are not limited to, prokaryotic, eukaryotic and Archaeal cells. Eukaryotic cells include, plant, fungal, protozoal and animal cells, including mammalian cells, primary cells and human cells.

C. Cloning

Facilitating dedifferentiation of target cells using ISWI-containing compositions will also increase cloning efficiency. For example, cloning of domestic and laboratory animals is typically accomplished by transplanting a cell or nucleus (usually embryonic), into an enucleated oocyte, with the expectation that an environment which allows for the development of a normal animal has been generated. General cloning strategies and techniques for nuclear transplantation are described for example in U.S. Pat. No. 6,011,197 and references cited therein. However, the efficiency of this type of nuclear transplantation is low, particularly when the nucleus to be transplanted is isolated from a somatic rather than an embryonic cell., Use of the compositions and methods described herein allows for increased efficiency of nuclear transplantation, , particularly for somatic cell nuclei. Exposure of nuclei to compositions comprising ISWI, ISWI-related proteins, or functional equivalents allows nuclei to be reprogrammed and/or dedifferentiated to varying degrees prior to, or coincident with, their transplantation.

D. Immortalization

Similarly, the compositions and methods described herein can be used to immortalize cells, for example to generate a cell line. Most cell isolated directly from nonembryonic tissues will only undergo a limited number of cell divisions in culture and thus cell lines cannot be established from them. Established cell lines are traditionally derived from a tumor (e.g., HeLa cells, Friend leukemia cells, etc.); from embryonic tissues (e.g., BHK cells); or from cells that have become immortalized as a result of having undergone transformation which causes the cells to behave in some respects as cancer cells (e.g., CHO cells). Collections and descriptions of known cell lines are available, for example, from the American Type Culture Collection (ATCC) in Manassas, Va. Using the ISWI-containing compositions disclosed herein, a somatic cell can be transformed into one possessing a dedifferentiated phenotype, thereby facilitating the generation of cell lines from a variety of tissues.

E. Differentiation

Certain cells, for example neoplastic cancer cells, are believed to be inappropriately dedifferentiated or immortalized in vivo. Immortalization of these cells allows them to divide indefinitely. Thus, the compositions and methods described herein also find use in facilitating differentiation of a target cell, for example by administering an effective amount of an inhibitor of ISWI function to the cell. Non-limiting examples of ISWI inhibitors include, antibodies (polyclonal and monoclonal); small molecules and the like. Further, as described in further detail below, ISWI functional components can be fused to one or more DNA binding molecules having known effect on gene(s) involved in differentiation.

Polynucleotide and Polypeptide Delivery

The observation that ISWI and related chromatin remodeling ATPases are capable of a removing basal transcription factor from its association with nuclear chromatin (leading to loss of the basal transcription factor from the nucleus) indicates that overexpression of ISWI in somatic nuclei (or somatic cells containing such nuclei) will dedifferentiate the nucleus, thereby increasing the efficiency by which such a nucleus will generate a live adult organism after transplantation into an egg. This will increase the efficiency of cloning using, for example, stably transformed cells.

Accordingly, in one embodiment, ISWI or a related chromatin remodeling ATPase is expressed in a somatic cell which is to be used as a donor of a nucleus for transplantation into an egg. The recipient egg can be enucleated, can have its nucleus inactivated, for example, by ultraviolet irradiation, or can have an intact nucleus. In a separate embodiment, purified nuclei can be incubated with ISWI or a related chromatin remodeling ATPase, prior to introduction of the nuclei into eggs.

The compositions described herein, comprising ISWI and/or a related chromatin remodeling ATPase, can be provided to the target cell in vitro or in vivo. In addition, the compositions can be provided as polypeptides, polynucleotides or combinations thereof.

A. Delivery of Polynucleotides

In certain embodiments, the compositions are provided as one or more polynucleotides. Further, as noted above, the ISWI-containing (or ISWI-inhibitor-containing) compositions may be designed as a fusion between a polypeptide DNA-binding domain and an ISWI-containing composition (or functional fragment thereof) and is encoded by a fusion nucleic acid. In both fusion and non-fusion cases, the nucleic acid can be cloned into intermediate vectors for transformation into prokaryotic or eukaryotic cells for replication and/or expression. Intermediate vectors for storage or manipulation of the nucleic acid or production of protein can be prokaryotic vectors, (e.g., plasmids), shuttle vectors, insect vectors, or viral vectors for example. An ISWI-containing (or inhibitor thereof) nucleic acid can also cloned into an expression vector, for administration to a bacterial cell, fungal cell, protozoal cell, plant cell, or animal cell, preferably a mammalian cell, more preferably a human cell.

To obtain expression of a cloned nucleic acid, it is typically subcloned into an expression vector that contains a promoter to direct transcription. Suitable bacterial and eukaryotic promoters are well known in the art and described, e.g., in Sambrook et al., supra; Ausubel et al., supra; and Kriegler, Gene Transfer and Expression: A Laboratory Manual (1990). Bacterial expression systems are available in, e.g., E. coli, Bacillus sp., and Salmonella. Palva et al (1983) Gene 22:229–235. Kits for such expression systems are commercially available. Eukaryotic expression systems for mammalian cells, yeast, and insect cells are well known in the art and are also commercially available, for example, from Invitrogen, Carlsbad, Calif. and Clontech, Palo Alto, Calif.

The promoter used to direct expression of the nucleic acid of choice depends on the particular application. For example, a strong constitutive promoter is typically used for expression and purification. In contrast, when a dedifferentiation protein is to be used in vivo, either a constitutive or an inducible promoter is used, depending on the particular use of the protein. In addition, a weak promoter can be used, such as HSV TK or a promoter having similar activity. The promoter typically can also include elements that are responsive to transactivation, e.g., hypoxia response elements, Ga14 response elements, lac repressor response element, and small molecule control systems such as tet-regulated systems and the RU-486 system. See, e.g., Gossen et al. (1992) Proc. Natl. Acad. Sci USA 89:5547–5551; Oligino et al.(1998) Gene Ther. 5:491–496; Wang et al (1997) Gene Ther. 4:432–441; Neering et al. (1996) Blood 88:1147–1155; and Rendahl et al. (1998) Nat. Biotechnol. 16:757–761.

In addition to a promoter, an expression vector typically contains a transcription unit or expression cassette that contains additional elements required for the expression of the nucleic acid in host cells, either prokaryotic or eukaryotic. A typical expression cassette thus contains a promoter operably linked, e.g., to the nucleic acid sequence, and signals required, e.g., for efficient polyadenylation of the transcript, transcriptional termination, ribosome binding, and/or translation termination. Additional elements of the cassette may include, e.g., enhancers, and heterologous spliced intronic signals.

The particular expression vector used to transport the genetic information into the cell is selected with regard to the intended use of the resulting dedifferentiation polypeptide, e.g., expression in plants, animals, bacteria, fungi, protozoa etc. Standard bacterial expression vectors include plasmids such as pBR322, pBR322-based plasmids, pSKF, pET23D, and commercially available fusion expression systems such as GST and LacZ. Epitope tags can also be added to recombinant proteins to provide convenient methods of isolation, for monitoring expression, and for monitoring cellular and subcellular localization, e.g., c-myc or FLAG.

Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

Some expression systems have markers for selection of stably transfected cell lines such as thymidine kinase, hygromycin B phosphotransferase, and dihydrofolate reductase. High-yield expression systems are also suitable, such as baculovirus vectors in insect cells, with a dedifferentiation nucleic acid sequence under the transcriptional control of the polyhedrin promoter or any other strong baculovirus promoter.

Elements that are typically included in expression vectors also include a replicon that functions in E. coli (or in the prokaryotic host, if other than E. coli), a selective marker, e.g., a gene encoding antibiotic resistance, to permit selection of bacteria that harbor recombinant plasmids, and unique restriction sites in nonessential regions of the vector to allow insertion of recombinant sequences.

Standard transfection methods can be used to produce bacterial, mammalian, yeast, insect, or other cell lines that express large quantities of dedifferentiation proteins, which can be purified, if desired, using standard techniques. See, e.g., Colley et al. (1989) *J. Biol. Chem.* 264:17619–17622; and *Guide to Protein Purification, in Methods in Enzymology*, vol. 182 (Deutscher, ed.) 1990. Transformation of eukaryotic and prokaryotic cells are performed according to standard techniques. See, e.g., Morrison (1977) *J. Bacteriol.* 132:349–351; Clark-Curtiss et al. (1983) in *Methods in Enzymology* 101:347–362 (Wu et al., eds).

Any procedure for introducing foreign nucleotide sequences into host cells can be used. These include, but are not limited to, the use of calcium phosphate transfection, DEAE-dextran-mediated transfection, polybrene, protoplast fusion, electroporation, lipid-mediated delivery (e.g., liposomes), microinjection, particle bombardment, introduction of naked DNA, plasmid vectors, viral vectors (both episomal and integrative) and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

Conventional viral and non-viral based gene transfer methods can be used to introduce nucleic acids into mammalian cells or target tissues. Such methods can be used to administer nucleic acids encoding reprogramming polypeptides to cells in vitro. Preferably, nucleic acids are administered for in vivo or ex vivo gene therapy uses. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. For reviews of gene therapy procedures, see, for example, Anderson (1992) *Science* 256:808–813; Nabel et al. (1993) *Trends Biotechnol.* 11:211–217; Mitani et al. (1993) *Trends Biotechnol.* 11:162–166; Dillon (1993) *Trends Biotechnol.* 11:167–175; Miller (1992) *Nature* 357:455–460; Van Brunt (1988) *Biotechnology* 6(10):1149–1154; Vigne (1995) *Restorative Neurology and Neuroscience* 8:35–36; Kremer et al. (1995) *British Medical Bulletin* 51(1):31–44; Haddada et al., in *Current Topics in Microbiology and Immunology*, Doerfler and Böhm (eds), 1995; and Yu et al. (1994) *Gene Therapy* 1:13–26.

Methods of non-viral delivery of nucleic acids include lipofection, microinjection, ballistics, virosomes, liposomes, immunoliposomes, polycation or lipid:nucleic acid conjugates, naked DNA, artificial virions, and agent-enhanced uptake of DNA. Lipofection is described in, e.g., U.S. Pat. Nos. 5,049,386; 4,946,787; and 4,897,355 and lipofection reagents are sold commercially (e.g., Transfectam™ and Lipofectin™). Cationic and neutral lipids that are suitable for efficient receptor-recognition lipofection of polynucleotides include those of Felgner, WO 91/17424 and WO 91/16024. Nucleic acid can be delivered to cells (ex vivo administration) or to target tissues (in vivo administration).

The preparation of lipid:nucleic acid complexes, including targeted liposomes such as immunolipid complexes, is well known to those of skill in the art. See, e.g., Crystal (1995) *Science* 270:404–410; Blaese et al. (1995) *Cancer Gene Ther.* 2:291–297; Behr et al. (1994) *Bioconjugate Chem.* 5:382–389; Remy et al. (1994) *Bioconjugate Chem.* 5:647–654; Gao et al. (1995) *Gene Therapy* 2:710–722; Ahmad et al. (1992) *Cancer Res.* 52:4817–4820; and U.S. Pat. Nos. 4,186,183; 4,217,344; 4,235,871; 4,261,975; 4,485,054; 4,501,728; 4,774,085; 4,837,028 and 4,946,787.

The use of RNA or DNA virus-based systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro, wherein the modified cells are administered to patients (ex vivo). Conventional viral based systems for the delivery of ZFPs include retroviral, lentiviral, poxviral, adenoviral, adeno-associated viral, vesicular stomatitis viral and herpesviral vectors. Integration in the host genome is possible with certain viral vectors, including the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, allowing alteration and/or expansion of the potential target cell population. Lentiviral vectors are retroviral vector that are able to transduce or infect non-dividing cells and typically produce high viral titers. Selection of a retroviral gene transfer system would therefore depend on the target tissue. Retroviral vectors have a packaging capacity of up to 6–10 kb of foreign sequence and are comprised of cis-acting long terminal repeats (LTRs). The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), simian immunodeficiency virus (SIV), human immunodeficiency virus (HIV), and combinations thereof. Buchscher et al. (1992) *J. Virol.* 66:2731–2739; Johann et al. (1992) *J. Virol.* 66:1635–1640; Sommerfelt et al. (1990) *Virol.* 176:58–59; Wilson et al. (1989) *J. Virol.* 63:2374–2378; Miller et al. (1991) *J. Virol.* 65:2220–2224; and PCT/US94/05700).

Adeno-associated virus (AAV) vectors are also used to transduce cells with target nucleic acids, e.g., in the in vitro production of nucleic acids and peptides, and for in vivo and ex vivo gene therapy procedures. See, e.g., West et al. (1987) *Virology* 160:38–47; U.S. Pat. No. 4,797,368; WO 93/24641; Kotin (1994) *Hum. Gene Ther.* 5:793–801; and Muzyczka (1994) *J. Clin. Invest.* 94:1351. Construction of recombinant AAV vectors are described in a number of publications, including U.S. Pat. No. 5,173,414; Tratschin et al. (1985) *Mol. Cell. Biol.* 5:3251–3260; Tratschin, et al. (1984) *Mol. Cell. Biol.* 4:2072–2081; Hermonat et al. (1984) *Proc. Natl. Acad. Sci. USA* 81:6466–6470; and Samulski et al. (1989) *J. Virol.* 63:3822–3828.

Recombinant adeno-associated virus vectors based on the defective and nonpathogenic parvovirus adeno-associated virus type 2 (AAV-2) are a promising gene delivery system. Exemplary AAV vectors are derived from a plasmid containing the AAV 145 bp inverted terminal repeats flanking a transgene expression cassette. Efficient gene transfer and stable transgene delivery due to integration into the genomes of the transduced cell are key features for this vector system. Wagner et al. (1998) *Lancet* 351(9117):1702–3; and Kearns et al (1996) *Gene Ther.* 9:748–55.

pLASN and MFG-S are examples are retroviral vectors that have been used in clinical trials. Dunbar et al. (1995) *Blood* 85:3048–305; Kohn et al. (1995) *Nature Med.* 1:1017–102; Malech et al (1997) *Proc. Natl. Acad. Sci. USA* 94:12133–12138. PA317/pLASN was the first therapeutic vector used in a gene therapy trial. (Blaese et al. (1995) *Science* 270:475–480. Transduction efficiencies of 50% or greater have been observed for MFG-S packaged vectors.

Ellem et al. (1997) *Immunol Immunother.* 44(1): 10–20; Dranoff et al. (1997) *Hum. Gene Ther.* 1:111–2.

In applications for which transient expression is preferred, adenoviral-based systems are useful. Adenoviral based vectors are capable of very high transduction efficiency in many cell types and are capable of infecting, and hence delivering nucleic acid to, both dividing and non-dividing cells. With such vectors, high titers and levels of expression have been obtained. Adenovirus vectors can be produced in large quantities in a relatively simple system.

Replication-deficient recombinant adenoviral (Ad) can be produced at high titer and they readily infect a number of different cell types. Most adenovirus vectors are engineered such that a transgene replaces the Ad E1a, E1b, and/or E3 genes; the replication defector vector is propagated in human 293 cells that supply the required E1 functions in trans. Ad vectors can transduce multiple types of tissues in vivo, including non-dividing, differentiated cells such as those found in the liver, kidney and muscle. Conventional Ad vectors have a large carrying capacity for inserted DNA. An example of the use of an Ad vector in a clinical trial involved polynucleotide therapy for antitumor immunization with intramuscular injection. Sterman et al (1998) *Hum. Gene Ther.* 7:1083–1089. Additional examples of the use of adenovirus vectors for gene transfer in clinical trials include Rosenecker et al. (1996) *Infection* 24:5–10; Sterman et al., supra; Welsh et al. (1995) *Hum. Gene Ther.* 2:205–218; Alvarez et al. (1997) *Hum. Gene Ther.* 5:597–613; and Topf et al. (1998) *Gene Ther.* 5:507–513.

Packaging cells are used to form virus particles that are capable of infecting a host cell. Such cells include 293 cells, which package adenovirus, and T2 cells or PA317 cells, which package retroviruses. Viral vectors used in gene therapy are usually generated by a producer cell line that packages a nucleic acid vector into a viral particle. The vectors typically contain the minimal viral sequences required for packaging and subsequent integration into a host, other viral sequences being replaced by an expression cassette for the protein to be expressed. Missing viral functions are supplied in trans, if necessary, by the packaging cell line. For example, AAV vectors used in gene therapy typically only possess ITR sequences from the AAV genome, which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment, which preferentially inactivates adenoviruses.

In many gene therapy applications, it is desirable that the gene therapy vector be delivered with a high degree of specificity to a particular tissue type. A viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al. (1995) *Proc. Natl. Acad. Sci. USA* 92:9747–9751 reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., $F_{ab}$ or $F_v$) having specific binding affinity for virtually any chosen cellular receptor. Although the above description applies primarily to viral vectors, the same principles can be applied to non-viral vectors. Such vectors can be engineered to contain specific uptake sequences thought to favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described infra. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a nucleic acid (gene or cDNA), and re-infused back into the subject organism (e.g., patient). Various cell types suitable for ex vivo transfection are well known to those of skill in the art. See, e.g., Freshney et al., *Culture of Animal Cells, A Manual of Basic Technique*, 3rd ed., 1994, and references cited therein, for a discussion of isolation and culture of cells from patients.

In one embodiment, hematopoietic stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ stem cells in vitro into clinically important immune cell types using cytokines such a GM-CSF, IFN-$\gamma$ and TNF-$\alpha$ are known. Inaba et al. (1992) *J. Exp. Med.* 176:1693–1702.

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panB cells), GR-1 (granulocytes), and Iad (differentiated antigen presenting cells). See Inaba et al., supra.

Vectors (e.g., retroviruses, adenoviruses, liposomes, etc.) containing therapeutic nucleic acids can be also administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention, as described below. See, e.g., *Remington's Pharmaceutical Sciences*, 17th ed., 1989.

B. Delivery of Polypeptides

In other embodiments, for example in certain in vitro situations, the target cells are cultured in a medium containing functional ISWI polypeptides, ISWI-inhibitors or function fragments of either ISWI polypeptide or ISWI-inhibitors.

An important factor in the administration of polypeptide compounds is ensuring that the polypeptide has the ability to traverse the plasma membrane of a cell, or the membrane of an intra-cellular compartment such as the nucleus. Cellular membranes are composed of lipid-protein bilayers that are freely permeable to small, nonionic lipophilic compounds and are inherently impermeable to polar compounds, macromolecules, and therapeutic or diagnostic agents. However, proteins, lipids and other compounds, which have the ability to translocate polypeptides across a cell membrane, have been described.

For example, "membrane translocation polypeptides" have amphiphilic or hydrophobic amino acid subsequences that have the ability to act as membrane-translocating carriers. In one embodiment, homeodomain proteins have the ability to translocate across cell membranes. The shortest internalizable peptide of a homeodomain protein, Antennapedia, was found to be the third helix of the protein, from amino acid position 43 to 58. Prochiantz (1996) *Curr. Opin. Neurobiol.* 6:629–634. Another subsequence, the h (hydrophobic) domain of signal peptides, was found to have similar cell membrane translocation characteristics. Lin et al (1995) *J. Biol. Chem.* 270:14255–14258.

Examples of peptide sequences which can be linked to an ISWI polypeptide for facilitating its uptake into cells include, but are not limited to: an 11 amino acid peptide of the tat protein of HIV; a 20 residue peptide sequence which corresponds to amino acids 84–103 of the p16 protein (see Fahraeus et al (1996) *Curr. Biol.* 6:84); the third helix of the 60-amino acid long homeodomain of Antennapedia (Derossi et al. (1994) *J. Biol. Chem.* 269:10444); the h region of a signal peptide, such as the Kaposi fibroblast growth factor (K-FGF) h region (Lin et al., supra); and the VP22 translocation domain from HSV (Elliot et al. (1997) *Cell* 88:223–233). Other suitable chemical moieties that provide enhanced cellular uptake can also be linked, either covalently or non-covalently, to the ISWI (or ISWI inhibitor) polypeptides.

Toxin molecules also have the ability to transport polypeptides across cell membranes. Often, such molecules (called "binary toxins") are composed of at least two parts: a translocation or binding domain and a separate toxin domain. Typically, the translocation domain, which can optionally be a polypeptide, binds to a cellular receptor, facilitating transport of the toxin into the cell. Several bacterial toxins, including *Clostridium perfringens* iota toxin, diphtheria toxin (DT), Pseudomonas exotoxin A (PE), pertussis toxin (PT), *Bacillus anthracis* toxin, and pertussis adenylate cyclase (CYA), have been used to deliver peptides to the cell cytosol as internal or amino-terminal fusions. Arora et al. (1993) *J. Biol. Chem.* 268:3334–3341; Perelle et al. (1993) *Infect. Immun.* 61:5147–5156; Stenmark et al. (1991) *J. Cell Biol.* 113:1025–1032; Donnelly et al. (1993) *Proc. Natl. Acad. Sci. USA* 90:3530–3534; Carbonetti et al. (1995) *Abstr. Annu. Meet. Am. Soc. Microbiol.* 95:295; Sebo et al. (1995) *Infect. Immun.* 63:3851–3857; Klimpel et al. (1992) *Proc. Natl. Acad. Sci. USA.* 89:10277–10281; and Novak et al. (1992) *J. Biol. Chem.* 267:17186–17193.

Such subsequences can be used to translocate polypeptides, including the polypeptides as disclosed herein, across a cell membrane. This is accomplished, for example, by derivatizing the fusion polypeptide with one of these translocation sequences, or by forming an additional fusion of the translocation sequence with the fusion polypeptide. Optionally, a linker can be used to link the fusion polypeptide and the translocation sequence. Any suitable linker can be used, e.g., a peptide linker.

A suitable polypeptide can also be introduced into an animal cell, preferably a mammalian cell, via liposomes and liposome derivatives such as immunoliposomes. The term "liposome" refers to vesicles comprised of one or more concentrically ordered lipid bilayers, which encapsulate an aqueous phase. The aqueous phase typically contains the compound to be delivered to the cell.

The liposome fuses with the plasma membrane, thereby releasing the compound into the cytosol. Alternatively, the liposome is phagocytosed or taken up by the cell in a transport vesicle. Once in the endosome or phagosome, the liposome is either degraded or it fuses with the membrane of the transport vesicle and releases its contents.

In current methods of drug delivery via liposomes, the liposome ultimately becomes permeable and releases the encapsulated compound at the target tissue or cell. For systemic or tissue specific delivery, this can be accomplished, for example, in a passive manner wherein the liposome bilayer is degraded over time through the action of various agents in the body. Alternatively, active drug release involves using an agent to induce a permeability change in the liposome vesicle. Liposome membranes can be constructed so that they become destabilized when the environment becomes acidic near the liposome membrane. See, e.g., *Proc. Natl. Acad. Sci. USA* 84:7851 (1987); *Biochemistry* 28:908 (1989). When liposomes are endocytosed by a target cell, for example, they become destabilized and release their contents. This destabilization is termed fusogenesis. Dioleoylphosphatidylethanolamine (DOPE) is the basis of many "fusogenic" systems.

For use with the methods and compositions disclosed herein, liposomes typically comprise a fusion polypeptide as disclosed herein, a lipid component, e.g., a neutral and/or cationic lipid, and optionally include a receptor-recognition molecule such as an antibody that binds to a predetermined cell surface receptor or ligand (e.g., an antigen). A variety of methods are available for preparing liposomes as described in, e.g.; U.S. Pat. Nos. 4,186,183; 4,217,344; 4,235,871; 4,261,975; 4,485,054; 4,501,728; 4,774,085; 4,837,028; 4,235,871; 4,261,975; 4,485,054; 4,501,728; 4,774,085; 4,837,028; 4,946,787; PCT Publication No. WO 91/17424; Szoka et al. (1980) *Ann. Rev. Biophys. Bioeng.* 9:467; Deamer et al. (1976) *Biochim. Biophys. Acta* 443:629–634; Fraley, et al. (1979) *Proc. Natl. Acad. Sci. USA* 76:3348–3352; Hope et al (1985) *Biochim. Biophys. Acta* 812:55–65; Mayer et al. (1986) *Biochim. Biophys. Acta* 858:161–168; Williams et al. (1988) *Proc. Natl. Acad. Sci. USA* 85:242–246; *Liposomes*, Ostro (ed.), 1983, Chapter 1); Hope et al. (1986) *Chem. Phys. Lip.* 40:89; Gregoriadis, *Liposome Technology* (1984) and Lasic, *Liposomes: from Physics to Applications* (1993). Suitable methods include, for example, sonication, extrusion, high pressure/homogenization, microfluidization, detergent dialysis, calcium-induced fusion of small liposome vesicles and ether-fusion methods, all of which are well known in the art.

In certain embodiments, it may be desirable to target a liposome using targeting moieties that are specific to a particular cell type, tissue, and the like. Targeting of liposomes using a variety of targeting moieties (e.g., ligands, receptors, and monoclonal antibodies) has been previously described. See, e.g., U.S. Pat. Nos. 4,957,773 and 4,603,044.

Examples of targeting moieties include monoclonal antibodies specific to antigens associated with neoplasms, such as prostate cancer specific antigen and MAGE. Tumors can also be diagnosed by detecting gene products resulting from the activation or overexpression of oncogenes, such as ras or c-erbB2. In addition, many tumors express antigens normally expressed by fetal tissue, such as the alphafetoprotein (AFP) and carcinoembryonic antigen (CEA). Sites of viral infection can be diagnosed using various viral antigens such as hepatitis B core and surface antigens (HBVc, HBVs) hepatitis C antigens, Epstein-Barr virus antigens, human immunodeficiency type-1 virus (HIV-1) and papilloma virus antigens. Inflammation can be detected using molecules specifically recognized by surface molecules which are expressed at sites of inflammation such as integrins (e.g., VCAM-1), selectin receptors (e.g., ELAM-1) and the like.

Standard methods for coupling targeting agents to liposomes are used. These methods generally involve the incorporation into liposomes of lipid components, e.g., phosphatidylethanolamine, which can be activated for attachment of targeting agents, or incorporation of derivatized lipophilic compounds, such as lipid derivatized bleomycin. Antibody targeted liposomes can be constructed using, for instance, liposomes which incorporate protein A. See Renneisen et al. (1990) *J. Biol. Chem.* 265:16337–16342 and Leonetti et al. (1990) *Proc. Natl. Acad. Sci. USA* 87:2448–2451.

Pharmaceutical Compositions and Administration

ISWI-containing polypeptides (or inhibitors thereof) as disclosed herein, and expression vectors encoding these polypeptides, can be used in conjunction with various methods of gene therapy to facilitate the action of a therapeutic gene product. In such applications, an ISWI polypeptide or ISWI inhibitor can be administered directly to a patient, e.g., to facilitate the modulation of gene expression and for therapeutic or prophylactic applications, for example, cancer, ischemia, diabetic retinopathy, macular degeneration, rheumatoid arthritis, psoriasis, HIV infection, sickle cell anemia, Alzheimer's disease, muscular dystrophy, neurodegenerative diseases, vascular disease, cystic fibrosis, stroke, and the like. Examples of microorganisms whose inhibition can be facilitated through use of the methods and compositions disclosed herein include pathogenic bacteria, e.g., Chlamydia, Rickettsial bacteria, Mycobacteria, Staphylococci, Streptococci, Pneumococci, Meningococci and Conococci, Klebsiella, Proteus, Serratia, Pseudomonas, Legionella, Diphtheria, Salmonella, Bacilli (e.g., anthrax), Vibrio (e.g., cholera), Clostridium (e.g., tetanus, botulism), Yersinia (e.g., plague), Leptospirosis, and Borrellia (e.g., Lyme disease bacteria); infectious fungus, e.g., Aspergillus, Candida species; protozoa such as sporozoa (e.g., Plasmodia), rhizopods (e.g., Entamoeba) and flagellates (Trypanosoma, Leishmania, Trichomonas, Giardia, etc.);viruses, e.g., hepatitis (A, B, or C), herpes viruses (e.g., VZV, HSV-1, HHV-6, HSV-II, CMV, and EBV), HIV, Ebola, Marburg and related hemorrhagic fever-causing viruses, adenoviruses, influenza viruses, flaviviruses, echoviruses, rhinoviruses, coxsackie viruses, comaviruses, respiratory syncytial viruses, mumps viruses, rotaviruses, measles viruses, rubella viruses, parvoviruses, vaccinia viruses, HTLV viruses, retroviruses, lentiviruses, dengue viruses, papillomaviruses, polioviruses, rabies viruses, and arboviral encephalitis viruses, etc.

Administration of therapeutically effective amounts of an ISWI polypeptides, ISWI inhibitors or a nucleic acid encoding an ISWI polypeptide (or inhibitor) is by any of the routes normally used for introducing polypeptides or nucleic acids into ultimate contact with the tissue to be treated. The polypeptides or nucleic acids are administered in any suitable manner, preferably with pharmaceutically acceptable carriers. Suitable methods of administering such modulators are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions. See, e.g., *Remington's Pharmaceutical Sciences*, 17$^{th}$ ed. 1985.

ISWI polypeptides (or inhibitors thereof) or nucleic acids, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Compositions can be administered, for example, by intravenous infusion, orally, topically, intraperitoneally, intravesically or intrathecally. The formulations of compounds can be presented in unit-dose or multi-dose sealed containers, such as ampoules and vials. Injection solutions and suspensions can be prepared from sterile powders, granules, and tablets of the kind known to those of skill in the art.

Assays for Chromatin Remodeling

The ISWI protein is an ATPase that is capable of remodeling chromatin. Accordingly, additional chromatin remodeling ATPases are also useful in the methods and compositions disclosed herein. Assays for chromatin remodeling, as well as assays for ATPase activity are well-known to those of skill in the art. Consequently, chromatin remodeling ATPases other than ISWI are contemplated by the present disclosure and are available to one of skill using established methods, some of which are set forth below.

Numerous activities of chromatin remodeling complexes have been described, including but not limited to the following. A characteristic activity of all chromatin remodeling complexes is nucleosome- or DNA-dependent ATPase activity. Chromatin remodeling complexes can facilitate binding of transcription factors to genes in a chromatin context and facilitate accessibility of sequences in chromatin to restriction enzymes and other nucleases. Certain remodeling complexes (those containing the ISWI ATPase) also possess the ability to assemble periodic nucleosome arrays (i.e. they are capable of spacing nucleosomes). Changes in DNA topology (i.e., degree of supercoiling) can also result from the action of chromatin remodeling complexes; these are believed to reflect either alterations of the path of DNA along the nucleosome or alterations in the path of linker DNA along the chromatin fiber. Chromatin remodeling complexes are also capable of transferring histones from chromatin to either DNA or protein acceptors. Stimulation of transcription initiation can also result from the action of chromatin remodeling complexes.

The various activities of chromatin remodeling complexes can be assayed by a number of techniques, as are known to those of skill in the art, and as have been described in publications disclosing the isolation and characterization of the various chromatin remodeling complexes, as set forth supra. See also Imblazano et al. (1994) *Nature* 370:481–485 and Cote et al. (1993) *Science* 265:53–60 for descriptions of assays involving facilitation of transcription factor binding. Assays involving nucleosome repositioning are described by, for example, Hamiche et al (1999) *Cell* 97:833–842 and Guschin et al. (2000) *Biochemistry* 39:5238–5245. Accordingly, it is possible for one of skill in the art to determine whether a given multiprotein complex is a chromatin remodeling complex and to determine whether a particular polypeptide is a component of a chromatin remodeling complex or functional fragment thereof. Additional examples of assays for chromatin remodeling activity are provided infra and in publications such as *Methods in Enzymology*, Vol. 304, "Chromatin" (P. M. Wassarman and A. P. Wolffe, eds.), Academic Press, San Diego, 1999; and *Methods in Molecular Biology*, Vol. 119, "Chromatin Protocols" (P. B. Becker, ed.) Humana Press, Totowa, 1999. See also U.S. Pat. No. 5,972,608.

An additional assay for chromatin modification is modulation of gene expression. Modulation of gene expression can be a direct result of chromatin remodeling, or it can result from binding of a molecule which modulates gene expression such as, for example, an endogenous or exogenous transcriptional regulatory molecule, to the remodeled chromatin. Assays for gene modulation (e.g., transcriptional activation and/or repression, reporter gene activity, measurement of protein levels) are well-known to those of skill in the art and are described, for example, in co-owned WO 00/41566.

Applications

The compositions and methods disclosed herein can be used to facilitate a number of processes involving cellular chromatin. These processes include, but are not limited to, dedifferentiation or differentiation of a target cell, cloning, creation of cell lineages, immortalization of cell, transcription, replication, recombination, repair, integration, maintenance of telomeres, and processes involved in chromosome stability and disjunction. Accordingly, the methods and compositions disclosed herein can be used to affect any of these processes, as well as any other process which can be influenced by the effect of ISWI and/or related chromatin remodeling ATPases on chromatin structure and DNA binding proteins.

In one embodiment, the compositions and methods disclosed herein are used to increase the efficiency of nuclear transfer to provide transplant tissue that is not subject to immune rejection by the recipient. See, e.g., Gurdon et al., supra. Obtaining a somatic nucleus from an individual in need of a tissue transplant, subjecting the nucleus to the action of ISWI or a related chromatin remodeling ATPase, transplanting such a treated nucleus into an egg, and development of the resultant transplant embryo, optionally in the presence of one or more differentiation factors, can lead to production of tissue suitable for transplant into the individual from whom the somatic nucleus was obtained. Since the tissue is derived from the transplant recipient, it will not stimulate an immune response, as would tissue from an unrelated donor. Such transplants can constitute solid organ transplants (e.g., heart, liver, kidney) or bone marrow transplants such as are used in the treatment of various malignancies such as, for example, leukemias and lymphomas. Such transplants can also be used in the treatment of, for example, neurological disorders, diabetes and the like.

The methods and compositions disclosed herein can also be used in processes such as, for example, therapeutic regulation of disease-related genes, engineering of cells for manufacture of protein pharmaceuticals, pharmaceutical discovery (including target discovery, target validation and engineering of cells for high throughput screening methods) and plant agriculture.

EXAMPLES

The following examples are presented as illustrative of, but not limiting, the claimed subject matter.

Example 1

Analysis of Protein Location and Nuclear Structure During Somatic Nuclei Remodeling The repartitioning of specific proteins and changes in nuclear structure during remodeling of nuclei from Xenopus somatic cells was first analyzed. To simplify nuclear remodeling assays by eliminating nuclear transport steps, both the plasma membrane and nuclear envelope of Xenopus XTC-2 cells (henceforth called nuclei) were permeabilized with a detergent, essentially as described in Adam et al. (1992) *Methods Enzymol.* 219:97–110. Xenopus XTC-2 cells were permeabilized with 30 µg/ml digitonin for three minutes using the LL-Bsa method (Gurdon (1976) *J. Embryol. Exp. Morphol.* 36:5235407) replacing lysolecithin (which caused tight aggregation of nuclei) by digitonin. The XTC-2 cells were derived from tadpole epithelia as described in Pudney et al. (1973) *Experientia* 29:466–467 and the cells were in the log phase of growth when used. The permeability of the nuclear envelope was monitored by the passive entry of fluorescence-labeled immunoglobulin G (150k Da) into the nuclei (Newmeyer et al. (1986) *J Cell Biol* 103:2091–2102). The nuclei were incubated in Xenopus egg S phase extract for two hours and isolated by centrifugation. Briefly, Xenopus egg S phase high speed extract was prepared as described in Smythe et al. (1991) *Methods Cell Biol* 35:449–468. The standard 28 µl assay contained $1 \times 10^5$ nuclei, 25 µl of egg extract and an energy-regenerating system, ERS (1 mM ATP, 1 mM GTP, 20 mM phosphocreatine and 100 µg/ml creatine phosphokinase).

After incubation for two hours at room temperature 100 µl of Buffer B (10 mM HEPES pH 7.8, 75 mM KCl, 4 mM magnesium chloride, 250 mM sucrose, 0.5 mM spermidine trihydrochloride, 0.15 mM spermine tetrahydrochloride, 1 mM dithiothreitol, 10 mM β-glycerophosphate, 1 µg/ml leupeptin, 2 µg/ml pepstatin A, 100 µM 4-(2-aminoethyl)-benzenesulfonyl fluoride, AEBSF) was added and the reaction mix was centrifuged at 15,000× g for 10 min. The pellet, called remodeled nuclei, was analyzed by immunoblotting using SuperSignal West Dura (Pierce, Rockford, Ill.) as a substrate of horseradish peroxidase. Sources of antibodies are as follows: TBP, TFIIB and TFIIFα (Santa Cruz, Santa Cruz, Calif.), ORC2 (M. L. DePamphilis, NIH), histone H2B (Chemicon, Temecula, Calif.), RNA polymerase II (Covance, Richmond, Calif.), topoisomerase II (Luke et al (1989) *Dev Biol* 136:459–468) and nucleolin (P. Bouvet at Centre National de la Recherche Scientifique, Toulouse, France). Such remodeled nuclei showed distinct patterns of protein composition depending on energy utilization (see FIGS. 1–5).

TBP is representative of a class of proteins excluded from the remodeled nuclei. By immunoblot TBP was undetectable in the extract (FIG. 1A, lane 2), indicating that all signal detected in this analysis was of nuclear origin. TBP was excluded from the nuclei in the presence of an energy regeneration system (ERS) (FIG. 1A, lane 4). This exclusion was inhibited by either ATP depletion by apyrase (FIG. 1A, lane 5) or inclusion of nonhydrolyzable ATP or GTP analogues (FIG. 1A, lanes 6 and 7). Because the detection limit for TBP in this assay was less than $10^4$ nuclei/lane (each lane contains $1 \times 10^5$ nuclei), this result indicates the remodeled nuclei lost greater than 90% of their total TBP. Although the DNA of the nuclei replicated in the extract, the exclusion of TBP did not require chromatin disassembly associated with DNA replication because neither aphidicholin nor arabinosylcytosine (both inhibitors of DNA replication) inhibited the loss of TBP (FIG. 1A, lanes 8 and 9). Furthermore, the loss of TBP was not due to mitotic chromosome condensation, as tested by phase contrast microscopic examination of the nuclear envelope, which showed that the nuclei enter S phase upon incubation in the egg extract.

ORC2, a component of the prereplicative complex, is representative of a second class of proteins which were incorporated into the nuclei from the extract independent of energy utilization or DNA replication (FIG. 1A, lanes 4–9). ORC2 accumulation in the nuclei was necessary for detection because this protein was not recovered on centrifugation of the extract alone (FIG. 1A, lane 1). Core histones of the remodeled nuclei were not degraded or released in the extract and histone H2B was used as a loading control for nuclei (Dimitrov and Wolffe (1996) *EMBO J* 15:5897–5906).

Figure 2A:
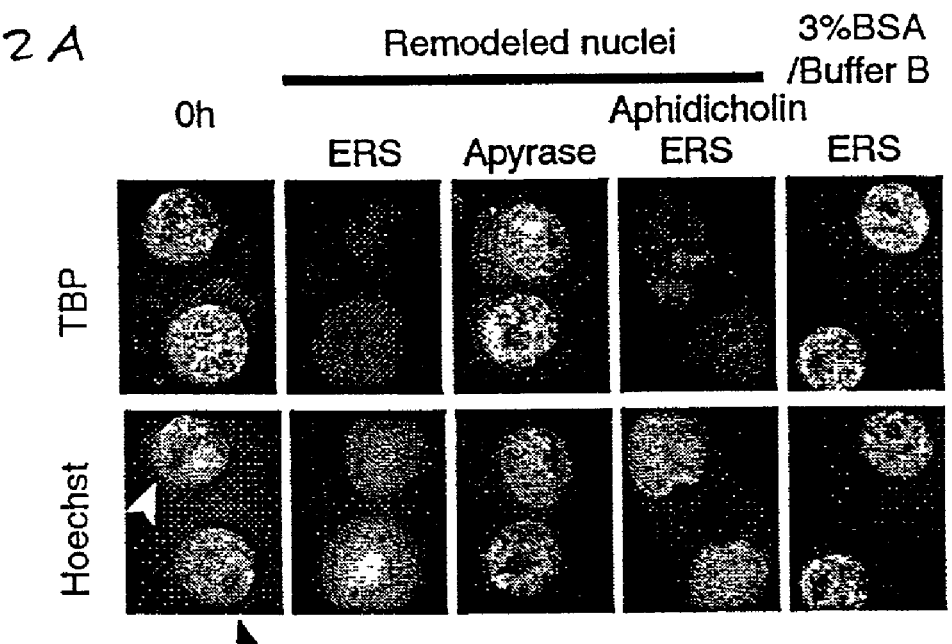
FIGS. 2A–B show analysis, by fluorescence microscopy, of somatic nuclei that have been incubated in egg extracts (Remodeled nuclei), compared with nuclei that had not been incubated in the egg extract (Oh) and control nuclei that were incubated in 3% BSA/Buffer B.
Figure 2B:
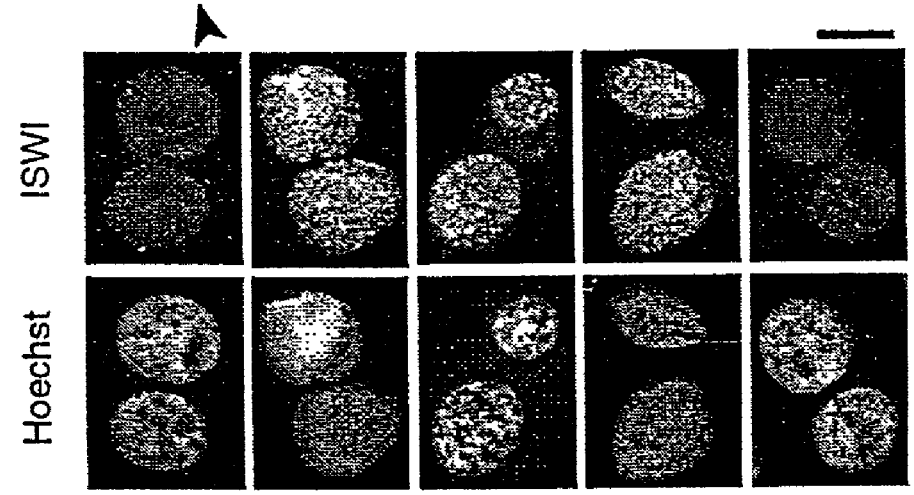
Figure 3:
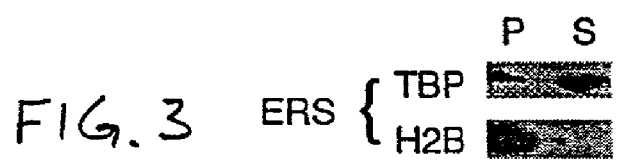
FIG. 3 shows detection of intact TBP in the supernatant after incubation of somatic nuclei in an egg extract. Pellets containing remodeled nuclei (P) and supernatant (S) were analyzed with antibodies to TBP or histone H2B, as indicated.

The behavior of other nuclear proteins was also analyzed in order to determine the nature of their distribution between nucleus and cytoplasm. The levels of linker histone H1, nucleolin, and the general transcription factor, TFIIB were diminished in the remodeled nuclei in the presence of ERS (FIG. 1B). Histone H1 is replaced with the egg type linker histone B4 by a molecular chaperone, nucleoplasmin (Dimitrov and Wolffe (1996) *EMBO J* 15:5897–5906). Nucleolin, located in the dense fibrillar component and granular component of the nucleolus, moderately decreased in the remodeled nuclei with ERS, which is consistent with the disappearance of the nucleoli (FIGS. 2A and 2B, ERS panels). Similar to ORC2, linker histone B4, nucleoplasmin, ISWI, and TFIIFα were incorporated into the remodeled nuclei (FIG. 1C). A third class of proteins including methyl-CpG binding protein 2 (MeCP2), topoisomerase II, histone deacetylase (Rpd3 and Sin3), and RNA polymerase II remained unchanged in abundance in the remodeled nuclei (FIG. 1D); this may reflect their stable association with the nuclear matrix (Li et al. (1996) *Biochem* 314:631–637).

To visualize the selective loss of nuclear components, nuclei were fixed prior to centrifugation and extract- and energy-dependent, but replication-independent exclusion of TBP was observed by immunofluorescence (FIG. 2A). The nuclei were fixed in the reaction mix with 4% paraformaldehyde and centrifuged onto a cover slip through a 30% sucrose cushion (Gorlich et al. (1994) *Cell* 79:767–778). TBP and ISWI were detected by TRITC-labeled secondary antibodies (Southern Biotechnologies, Birmingham, Ala.) as described (Spector et al. in "*Cells: A Laboratory Manual*" (Cold Spring Harbor Laboratory Press, New York, 1997) pp. 105.1–105.4). DNA was counterstained with Hoechst 33342. The nuclei clearly retained their integrity, although their chromatin became decondensed and dispersed (FIG. 2A, ERS and Aphidicholin/ERS panels). Nucleoli are greatly diminished in size in the presence of ERS (FIG. 2A). Loss of TBP from nuclei required the presence of egg extract, as the nuclei did not lose TBP in an inert protein solution, bovine serum albumin (BSA)/Buffer B. The incorporation of ISWI into nuclei was also monitored by immunofluorescence. As for active TBP removal, the pattern of passive incorporation of ISWI is identical whether monitored by immunoblot or microscopy (FIG. 2B).

Example 2

Removal of TBP from Remodeled Nuclei is Concentration-Dependent and Does Not Result in Degradation of TBP TBP was used as a specific molecular marker for nuclear remodeling. TBP is a fundamental component of the general transcription machinery required for transcription by all three RNA polymerases (Hernandez (1993) *Genes Dev* 7:1291–1308). Its loss from somatic nuclei reflects dynamic transitions in nuclear function and structure. Because TBP is undetectable in the egg extract, consistent with previous studies (Veenstra et al. (1999) *Mol Cell Biol* 19:7972–7982), somatic nuclei supply >99% of this protein, simplifying interpretation of the results. TBP released from the remodeled nuclei was readily detectable in the supernatant (FIG. 3) indicating that degradation of TBP did not account for removal from the nuclei. Thus, Xenopus egg extract contains the activity(ies) needed to reorganize specific nuclear structures and selectively remove TBP from chromosomes in an energy-dependent manner, leaving both TBP and nuclear integrity intact. This activity directing removal of TBP from the nuclear infrastructure is not abundant in the egg extract, since two-fold dilution of the extract with BSA results in loss of the activity.

Example 3

Reconstitution of Nuclear Remodeling Activity by ISWI

The activity(ies) in the egg which direct the release of TBP from chromatin were fractionated and analyses indicated that ISWI-containing fractions released TBP from nuclei. ISWI is a member of the SWI2/SNF2 superfamily and is the common catalytic subunit of at least three distinct ATP-dependent chromatin remodeling complexes enriched in *Drosophila* eggs and embryos (Tsukiyama et al. (1995) *Cell* 83:1021–1026; Ito et al. (1997) *Cell* 90:145–155; Varga-Weisz et al. (1997) *Nature* 388:598–602; Corona et al. (1999) *Mol Cell* 3:239–245; Hamiche et al. (1999) *Cell* 97:833–842). These complexes mobilize nucleosomes utilizing the energy derived from ATP hydrolysis, and the ISWI subunit per se is also capable of remodeling chromatin. ISWI is the most abundant nucleosome-dependent ATPase activity in the Xenopus egg extract; therefore, the contribution of its chromatin remodeling activities to the release of TBP from chromatin was tested.

Figure 4A:
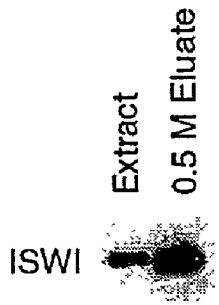
FIGS. 4A–D depict purification and biochemical characterization of ISWI from Xenopus egg extracts, and show that nucleosomal ATPase ISWI is competent to reconstitute nuclear remodeling activity in a biochemical complementation assay.
Figure 4B:
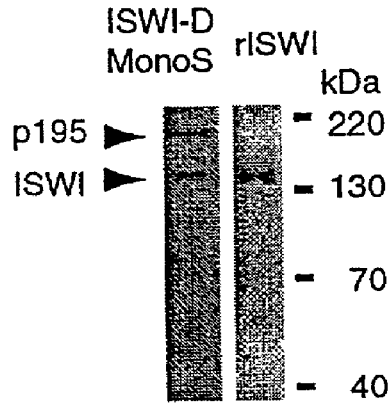

The ISWI-D complex was purified from Xenopus egg extract (FIG. 4A), and shown to contain two subunits: p195 and ISWI (FIG. 4B). For the purification, egg extract was fractionated through BioRex 70 (Bio-Rad, Hercules, Calif.) and MonoQ (Amersham Pharmacia, Piscataway, N.J.) essentially as described in Wade et al. (1998) *Curr Biol* 8:843–846. The MonoQ ISWI-D peak (eluting at approximately 0.45 M NaCl) was further purified by gradient elution on MonoS (linear gradient from 0.1 to 0.5 M NaCl in Buffer A) as described in Wade et al., supra. ISWI-D was eluted at approximately 0.3 M NaCl. *Drosophila* rISWI was produced in *E. coli* and purified by IMPACT T7 system (New England Biolabs, Beverly, Mass.) and Superdex 200 gel filtration column (Amersham Pharmacia). ATPase activity was tested as described in Corona et al, supra.

Figure 4C:
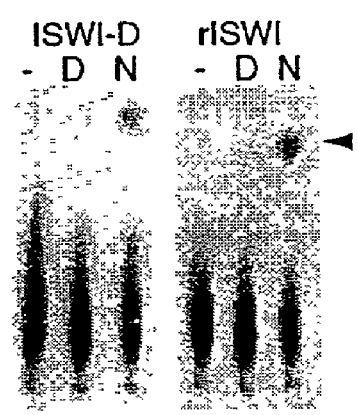
Figure 4D:
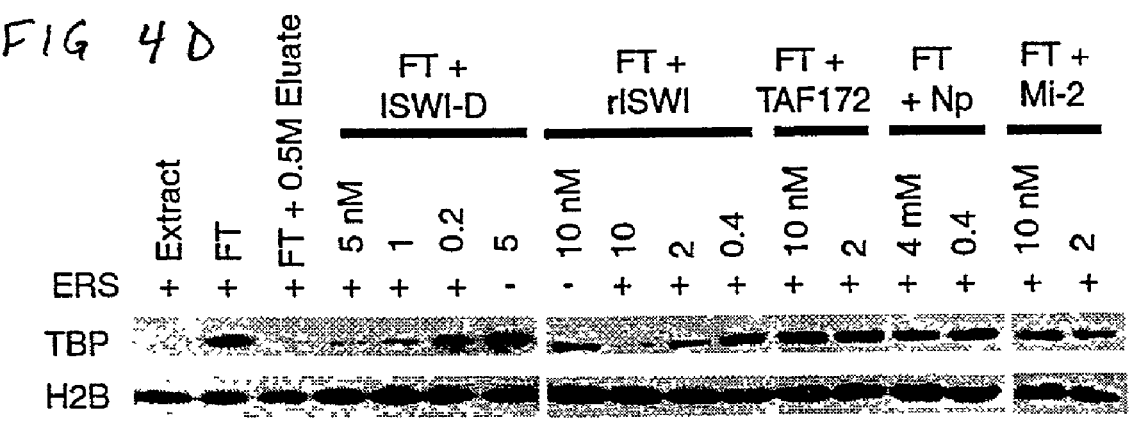

The ISWI-D complex is a nucleosomal ATPase comparable to recombinant ISWI (rISWI) from *Drosophila* (FIG. 4C). Either ISWI-D complex or rISWI were essential for release of TBP from nuclei. The endogenous activity in the extract responsible for the release of TBP from chromatin was depleted by applying the extract to SP Sepharose, and restored by combining the SP Sepharaose flow through (FT) and the 0.5 M NaCl eluate from BioRex 70 that contained ISWI (FIG. 4D, lanes 2 and 3). FT was prepared from SP Sepharose (Amersham Pharmacia) by equilibrating the resin with Buffer A and briefly centrifuging to deplete the buffer. The egg extract was incubated with the equilibrated resin for 30 minutes in a cold room and briefly centrifuged to collect FT. Either the purified ISWI-D complex or rISWI alone, at nanomolar concentrations, were competent to reconstitute release of TBP from nuclei when combined with FT in the presence of ERS (FIG. 4D, lanes 4–7 and 8–11). Release of TBP from nuclei by ISWI plus FT was also confirmed by immunofluorescence. As a negative control, a mutant of rISWI, in which lysine 159 in the adenine nucleotide binding domain was replaced with arginine (Corona et al., supra), lacked nucleosomal ATPase activity and was not competent to reconstitute release of TBP from nuclei. Neither the ISWI-D complex nor rISWI could release TBP from nuclei in the absence of FT.

Three other proteins known to modify protein-DNA interactions (TAF172, the Mi-2 complex and nucleoplasmin) were also tested in this biochemical complementation assay. Recombinant human TAF172 was prepared in a baculovirus expression system (see Chicca et al. (1998) *Mol Cell Biol* 18:1701–1710), while the Mi-2 complex and nucleoplasmin were isolated from Xenopus egg extracts. TAF 172, the human homologue of yeast Mot1, also belongs to the SWI2/SNF2 superfamily and removes TBP from DNA in vitro (Auble et al. (1994) *Genes Dev* 8:1920–1934; Chicca et al., supra). The Xenopus Mi-2 complex contains Mi-2, also a member of the SWI2/SNF2 superfamily, in addition to five other subunits and remodels chromatin (Wade et al (1998) *Curr Biol* 8:843–846; Guschin et al. (2000) *Biochem* 39:5238–5245). Nucleoplasmin remodels sperm chromatin upon fertilization (Dimitrov et al., supra; Philpott et al. (2000) *Cell* 69:759767). None of these proteins proved capable of reconstituting TBP removal activity when combined with the SP Sepharose FT fraction (FIG. 4D, lanes 12–17). Higher concentrations of these proteins were also tested, with similar results.

Because nucleoplasmin is capable of decondensing sperm chromatin, its ability to substitute for the FT fraction, to release TBP from nuclei in combination with ISWI, was tested. However, the combination of nucleoplasmin with either ISWI-D or rISWI was incapable of releasing TBP from nuclei.

Thus, ISWI can release TBP from chromatin by a specific and active mechanism in the presence of other proteins derived from the egg. Importantly, nucleoplasmin, TAF 172 and the Mi-2 complex were unable to reconstitute TBP release activity. Furthermore, the combination of ISWI and the SP Sepharose FT fraction, active in releasing TBP, was unable to release other proteins, which are released upon incubation of nuclei in the egg extract (see FIG. 1B). These results underscore the specific contribution of the chromosome remodeling factor ISWI to the global reorganization of somatic nuclei.

Example 4

Destablization of the Nuclear Matrix by ISWI

To understand the mechanism of the release of TBP further, nuclear matrix was prepared from the nuclei that had not been incubated in the egg extract, by using 0.5% Triton X-100, DNase I, 250 mM ammonium sulfate, and 2M NaCl. The nuclear matrix was prepared essentially as described D. L. Spector and D. Goldman, L. L. A, in *Cells, A Laboratory Manual*. (Cold Spring Harbor Laboratory Press, New York, 1997) pp. 44.1–44.8. Briefly, after the remodeled nuclei were isolated, soluble protein was extracted by cytoskeletal buffer (10 mM PIPES pH 6.8, 300 mM sucrose, 100 mM NaCl, 3 mM $MgCl_2$, 1 mM EGTA 1 mM AEBSF, 2 mM vanadyl riboside complex (VRC), 0.5% Triton X-100) and extraction buffer (10 mM PIPES pH 6.8, 250 mM ammonium sulfate, 300 mM sucrose, 3 mM $MgCl_2$, 1 mM EGTA, 1 mM AEBSF, 2 mM VRC) for 5 min each. To remove chromatin, the insoluble fraction was digested with DNase I buffer (10 mM PIPES pH 6.8, 300 mM sucrose, 50 mM NaCl, 3 mM $MgCl_2$, 1 mM EGTA, 1 mM AEBSF, 2 mM VRC, 0.5% Triton X-100, 400 units/ml DNase I) at 32° C. for 50 min. After washing with extraction buffer twice, the insoluble fraction was further treated with 2M NaCl buffer (10 mM PIPES pH 6.8, 300 mM sucrose, 2M NaCl, 3 mM $MgCl_2$, 1 mM EGTA, 1 mM AEBSF, 2 mM VRC) for 5 min. The pellet is the nuclear matrix.

Approximately 30% of total TBP and about 20% of histone H2B were recovered with the nuclear matrix (FIG. 5, lane 1), which is roughly consistent with a previous report of Kimura et al. (1999) *Mol Cell Biol* 19:5383–5392. Approximatley 15% of total DNA is recovered in the nuclear matrix preparation. Thus a major fraction of intranuclear TBP was tightly bound to the nuclear matrix itself or to chromatin associated with the nuclear matrix.

Figure 5:
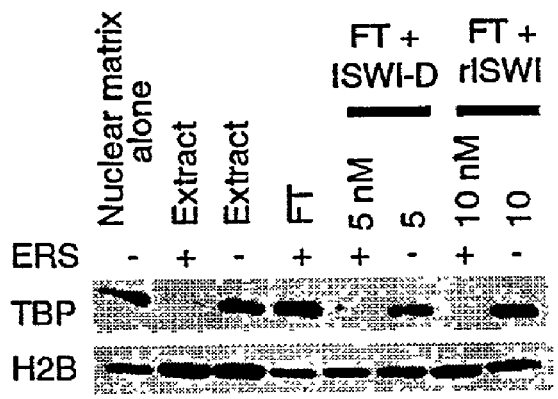
FIG. 5 shows analysis, by immunoblotting, of the association of TBP with the nuclear matrix. Analysis of histone H2B is shown as a control. Nuclear matrix was prepared as described in the Examples, and nuclear matrix proteins were separated by gel electorphoresis. Each lane contained matrix from $4 \times 10^5$ nuclei. The gel was blotted, and the blots were analyzed with antibodies to TBP or H2B. Nuclei were incubated with egg extract (lanes 2 and 3) or various combinations of proteins and protein fractions (lanes 4–8) prior to preparation of nuclear matrix. Analysis of a preparation of nuclear matrix from nuclei that were not incubated with extract or proteins is shown in lane 1. Presence or absence of an ERS in the incubation is indicated by "+" and "−," respectively.

The purified nuclear matrix was incubated in the egg extract and its composition was analyzed by immunoblotting. Whoe extract, in the presence of an ERS, was capable of releasing TBP from the nuclear matrix (FIG. 5, lanes 2 and 3). When the nuclear matrix was incubated in the presence of the FT fraction and an ERS, TBP was not released (FIG. 5, lane 4). However, addition of ISWI-D or rISWI to the FT fraction resulted in release of TBP (FIG. 5, lanes 5–8).

Thus, ISWI efficiently released TBP, even when it was tightly bound to the nuclear infrastructure. The mobilization of TBP from the nuclear matrix is consistent with the capacity of ISWI to destabilize even strong interactions such as those between histones and DNA. Both rISW- and ISWI-containing complexes are capable of mobilizing histone octamers along a linear DNA molecule in an ATP-dependent fashion Thus, the capacity of ISWI to destabilize and/or mobilize chromatin may underlie the dissolution of chromatin/TBP association with the nuclear matrix. Once the nuclear matrix has been disrupted, other activities in the egg might aid in the further displacement of TBP from DNA.

Example 5

Assays for Chromatin Remodeling Complexes

Methods for the purification, assay and characterization of various chromatin remodeling complexes are well-known to those of skill in the art. See, for example, *Methods in Enzymology*, Vol. 304, "Chromatin" (P. M. Wassarman and A. P. Wolffe, eds.), Academic Press, San Diego, 1999; and *Methods in Molecular Biology*, Vol. 119, "Chromatin Protocols" (P.B. Becker, ed.) Humana Press, Totowa, 1999.

Chromatin remodeling can take the form of, for example, deposition, removal or repositioning of nucleosomes within chromatin. Means for detecting chromatin remodeling include, but are not limited to, detecting changes in accessibility of specific sites in chromatin to sequence-specific nucleases such as restriction enzymes, determination of the appearance or disappearance of a regularly repeating pattern of chromatin digestion by non-sequence specific endonucleases such as micrococcal nuclease and DNase I, determination of nucleosome spacing, and nucleosome-binding assays. Also, as mentioned supra, chromatin remodeling complexes possess ATPase activity; therefore ATP hydrolysis assays can be used in the identification and/or characterization of chromatin remodeling complexes.

Restriction endonuclease accessibility assays are described by Logie et al., supra and Varga-Weisz et al. (1999) *Meth. Enzymology* 304:742–757. Assays for nucleosome spacing, DNase I accessibility, ATPase activity and nucleosome binding are disclosed by Varga-Weisz et al., supra. Assays to detect facilitation of transcription factor binding are described by Cote et al. (1994) *Science* 265:53–60 and Kwon et al. (1994) *Nature* 370:477–481. Assays for nucleosome repositioning (i.e., "sliding") are disclosed by Hamiche et al. (1999) *Cell* 97:833–842.

These assays, and others, can be used for the purification and characterization of chromatin remodeling complexes from various species, for example, the yeast SWI/SNF complex (Logie et al., supra), the *Drosophila* CHRAC complex (Varga-Weisz et al., supra) and the *Drosophila* NURF complex (Sandaltzopoulos et al., supra).

Example 6

ATPase Assay

Chromatin remodeling complexes utilize the energy of ATP hydrolysis to modify chromatin structure. Consequently, nucleosome- or DNA-dependent ATPase activity can be used to assay for a chromatin remodeling complex.

Methods and compositions for conducting ATPase assays are well-known to those of skill in the art. One measure of ATPase activity is the release of labeled pyrophosphate from $\gamma$-$^{32}$P-labeled ATP. Release is measured as the amount of radioactivity that does not bind to activated charcoal in 20 mM phosphoric acid.

An alternative method for measuring pyrophosphate release is to measure labeled pyrophosphate directly by thin layer chromatography. The reaction mixture contains 0.02 µg/ml DNA (or reconstituted nucleosomal array, see Example 11 infra), 5 nM SWI/SNF complex (or any other known or putative chromatin remodeling complex), 20 mM Tris, pH 8.0, 5 mM $MgCl_2$, 0.2 mM dithiothreitol, 0.1% Tween, 5% glycerol, 100 µg/ml bovine serum albumin, 100 µM ATP, and 0.2 µCi ($\gamma$-$^{32}$P)ATP (3 Ci/mmol) in a final volume of 20 µl and is incubated at 37° C. At the conclusion of the assay (under these conditions the reaction rate is linear for 5–10 minutes), 1 µl is pipetted onto a polyethyleneimine cellulose sheet and the sheet is developed in a solution of 0.75 M potassium phosphate, pH 3.5. In this system, ATP and pyrophosphate are clearly resolved from each other and from the origin. Quantitation is carried out either by autoradiography followed by excision and scintillation counting of labeled spots, or by phosphorimaging.

The preceding methods are adapted from those described by Logie et al. (1999) *Meth. Enzymology* 304:726–741.

An alternative solvent for thin-layer chromatography is 0.5 M LiCl/1 M formic acid. In this system, pyrophosphate is separated from unhydrolyzed ATP, which remains at the origin. Varga-Weisz et al. (1999) *Meth. Enzymol.* 304:742–757.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A method for facilitating cloning, the method comprising:
    (a) contacting an isolated non-human somatic cell with a polynucleotide, wherein the polynucleotide encodes a member of the ISWI, SWI/SNF or Mi-2/CHD family of polypeptides, and wherein the polypeptide is expressed in the cell and remodels the somatic nucleus;
    (b) isolating the remodeled somatic nucleus; and
    (c) introducing the somatic nucleus of step (b) into an enucleated non-human oocyte.

2. The method of claim 1, wherein the somatic nucleus and enucleated oocyte are obtained from an animal.

3. The method of claim 1, wherein the polypeptide is selected from the group consisting of SWI2/SNF2, STH1, BRM, hBRM, BRG1, Mi-2/CHD, ISW2 and hSNF2h.

4. A method of facilitating dedifferentiation of an isolated target cell, the method comprising the step of contacting the cell with a polynucleotide, wherein the polynucleotide encodes a member of the ISWI, SWIISNF or Mi-2/CHD family of polypeptides, and wherein the polypeptide is expressed in the cell and remodels the somatic nucleus.

5. The method of claim 4, wherein the cell is a eukaryotic cell.

6. The method of claim 5, wherein the cell is an animal cell.

7. The method of claim 4, wherein the polypeptide is selected from the group consisting of SWI2/SNF2, STH1, BRM, hBRM, BRG1, Mi-2/CHD, ISW2 and hSNF2h.

8. A method of facilitating nuclear transplantation, the method comprising the following steps:
    (a) contacting an isolated non-human somatic cell with a composition comprising a polynucleotide, wherein the polynucleotide encodes a member of the ISWI, SWISNF or Mi-2/CHD family of polypeptides;
    (b) isolating the nucleus from the cell of step (a); and
    (c) introducing the nucleus of step (b) into a non-human oocyte.

9. The method of claim 8, wherein the somatic nucleus is obtained from an animal.

10. The method of claim 8, wherein the polypeptide is selected from the group consisting of SWI2/SNF2, STH1, BRM, hBRM, BRG1, Mi-2/CHD, ISW2 and hSNF2h.

* * * * *